United States Patent [19]

Kirst et al.

[11] Patent Number: 5,229,362

[45] Date of Patent: Jul. 20, 1993

[54] ANTIBIOTIC A10255 COMPLEX AND FACTORS, AND PROCESS AND PRODUCTION THEREFOR

[75] Inventors: Herbert A. Kirst; Karl H. Michel, both of Indianapolis, Ind.

[73] Assignee: Eli Lilly and Company, Indianapolis, Ind.

[21] Appl. No.: 732,347

[22] Filed: Jul. 17, 1991

Related U.S. Application Data

[63] Continuation-in-part of Ser. No. 284,229, Dec. 14, 1988, abandoned, which is a continuation-in-part of Ser. No. 120,432, Nov. 13, 1987, abandoned, which is a continuation-in-part of Ser. No. 941,894, Dec. 15, 1986, abandoned.

[51] Int. Cl.$^5$ .................... A61K 37/02; A61K 35/74; C07K 7/54; C12P 21/00
[52] U.S. Cl. .......................... 514/9; 514/11; 530/317; 530/323; 424/117; 424/118; 426/635; 435/71.3; 435/170; 435/822
[58] Field of Search .............. 530/317, 323; 514/9, 514/11; 435/71.3, 170, 822; 426/635; 424/117, 118

[56] References Cited

U.S. PATENT DOCUMENTS 3,689,639  9/1972  Bergy et al. .................. 424/117
4,333,923  6/1982  Beck et al. ..................... 424/115

FOREIGN PATENT DOCUMENTS 0112233  6/1984  European Pat. Off. .
0274873  7/1988  European Pat. Off. .

OTHER PUBLICATIONS

J. M. Liesch and K. L. Rinehart, "Berninamycin 3. Total Structure of Berninamycin A", *J. Am. Chem. Soc.*, 99:5, Mar. 2, 1977.

*Primary Examiner*—Y. Christina Chan
*Attorney, Agent, or Firm*—Steven A. Fontana; Leroy Whitaker; Nancy J. Harrison

[57] ABSTRACT

Newly-discovered antibiotic A10255 factors B, C, E, F, G, H, and J are produced by submerged aerobic fermentation of *Streptomyces gardneri* NRRL 15537 and NRRL 18260 or an A10255-producing variant or mutant thereof. The antibiotics are active against a wide variety of pathogenic bacteria, and also enhance feed-utilization efficiency in chickens, weanling pigs, cattle and sheep. The antibiotics can also be used to detect the thiostrepton-resistance gene in Streptomyces species.

20 Claims, 7 Drawing Sheets

ANTIBIOTIC A10255 COMPLEX AND FACTORS, AND PROCESS AND PRODUCTION THEREFOR

REFERENCES TO COPENDING APPLICATION

This application is a continuation-in-part of application Ser. No. 07/284,229, filed on Dec. 14, 1988 (now abandoned) which is a continuation-in-part of application Ser. No. 07/120,432, filed on Nov. 13, 1987 (now abandoned), which is a continuation-in-part of application Ser. No. 06/941,894, filed on Dec. 15, 1986 (now abandoned).

SUMMARY OF THE INVENTION

This invention relates to newly-discovered antibiotic substances which are arbitrarily generically designated herein as antibiotic A10255. Antibiotic A10255 is composed of a mixture of at least 7 separate compounds or factors (factors B, C, E, F, G, H, and J). The mixture of factors is co-produced by culturing the novel strains *Streptomyces gardneri*, NRRL 15537 or NRRL 18260 or an A10255-producing mutant thereof, under submerged aerobic fermentation conditions until a substantial level of antibiotic A10255 is produced. The coproduced factors B, C, E, F, G, H, and J are extracted from the fermentation broth (in minor amounts) and from the mycelia (in major amounts) with solvents. The coproduced factors are separated as a mixture by concentrating the extracts and drying the resulting complex-containing precipitate. It should be noted that the term "antibiotic complex", and "A10255 complex" as used in the fermentation art and in this specification does not refer to a covalently-bonded chemical complex, but to a mixture of co-produced individual antibiotic factors. As will be recognized by those familiar with antibiotic fermentation, the ratio of individual factors produced in an antibiotic complex may vary, depending on the fermentation conditions used. The A10255 complex is further purified and is separated into individual factors B, C, E, F, G, H, and J by a series of chromatographic procedures.

Antibiotic A10255 complex and the individual factors B, C, E, F, G, H, and J inhibit the growth of microorganisms pathogenic to man and animals. The A10255 complex and the individual factors also increase feed utilization efficiency in chickens, cattle, sheep, and promote the growth and increase the feed utilization efficiency of weanling pigs.

Further aspects of the instant invention include the biologically pure cultures of the microorganisms *Streptomyces gardneri* NRRL 15537 and *Streptomyces gardneri* NRRL 18260, or an A10255-producing mutant thereof, and the methods for producing the A10255 complex. The invention also provides feed compositions comprising the A10255 complex or the individual A10255 factors combined with the appropriate feed for chickens, weanling pigs, sheep and cattle. Also, the invention encompasses various pharmaceutical compositions comprising a suitable vehicle and a therapeutically effective amount of the A10255 complex or of an individual factor thereof.

The A10255 complex of this invention can be used to select Streptomyces cells which have the thiostrepton-resistance gene.

DESCRIPTION OF THE DRAWINGS

The infrared absorption spectra of individual A-10255 factors B, C, E, F, G, H, and J run in KBr discs are presented in the drawings as follows.

DETAILED DESCRIPTION OF THE INVENTION

The A10255 complex, comprised mainly of factors B, C, E, F, G, H, and J is produced by culturing in an aqueous culture medium containing assimilable sources of carbohydrate, nitrogen and inorganic salts the heretofore undescribed strains of *Streptomyces gardneri*, strain NRRL 15537 or NRRL 18260, or an A10255-producing mutant thereof, until the A10255 complex is produced.

As is the case with many antibiotic-producing cultures, fermentation of an A10255-producing strain of *S. gardneri* NRRL 15537 or NRRL 18260 results in the coproduction of a number of antibiotic substances. Antibiotic A10255 factor B is the major factor produced by the NRRL 15537 culture, and factors C, E, F, G, H, and J are produced in minor yet isolable amounts. Other factors either are present in such minor quantities as to render their isolation unrewarding or are relatively unstable. Factors G and H have been isolated from fermentation of the NRRL 18260 culture, with factor G being the major factor. The amounts of the individual factors coproduced may vary from fermentation to fermentation of any of the above-described microorganisms.

The antibiotic factors B, C, E, F, G, H, and J, coproduced during the fermentation and obtained as a mixture, are termed the A10255 complex. The individual factors are separated from each other and isolated as distinct entities with the following physical and biological properties.

PHYSICAL CHARACTERISTICS OF THE ANTIBIOTIC FACTORS

A10255 Factor B

A10255 Factor B is a non-crystalline white to light-yellow powder which is soluble in dimethylsulfoxide, dimethylformamide, pyridine, chloroform/methanol mixtures, and 4:1 (v:v) tetrahydrofuran:water.

Elemental analysis of factor B indicates the following approximate percentage composition (average): carbon, 49.25%; hydrogen, 3.94%; nitrogen, 15.65%; oxygen, 21.36%; and sulfur, 6.73%.

The apparent molecular weight of A10255 factor B was determined by fast atom bombardment mass spectrometry to be approximately 1244 daltons.

Electrometric titration of A10255 factor B in 66% aqueous dimethylformamide indicates the presence of three titratable groups with pKa values of 4.9, 11.2, and 12.8.

Amino acid analysis of factor B (after hydrolysis with 6N hydrochloric acid) indicates the presence of ammonia (5,268 mmoles/mg) and threonine (629 mmoles/mg). The analysis also evinced a large, unidentified peak coming before the position for the histidine peak.

The ultraviolet absorption spectrum for factor B obtained in neutral, acidic, and basic methanol demonstrated $\lambda_{max}$ of 245 nm ($\epsilon=66,000$).

Figure 1:
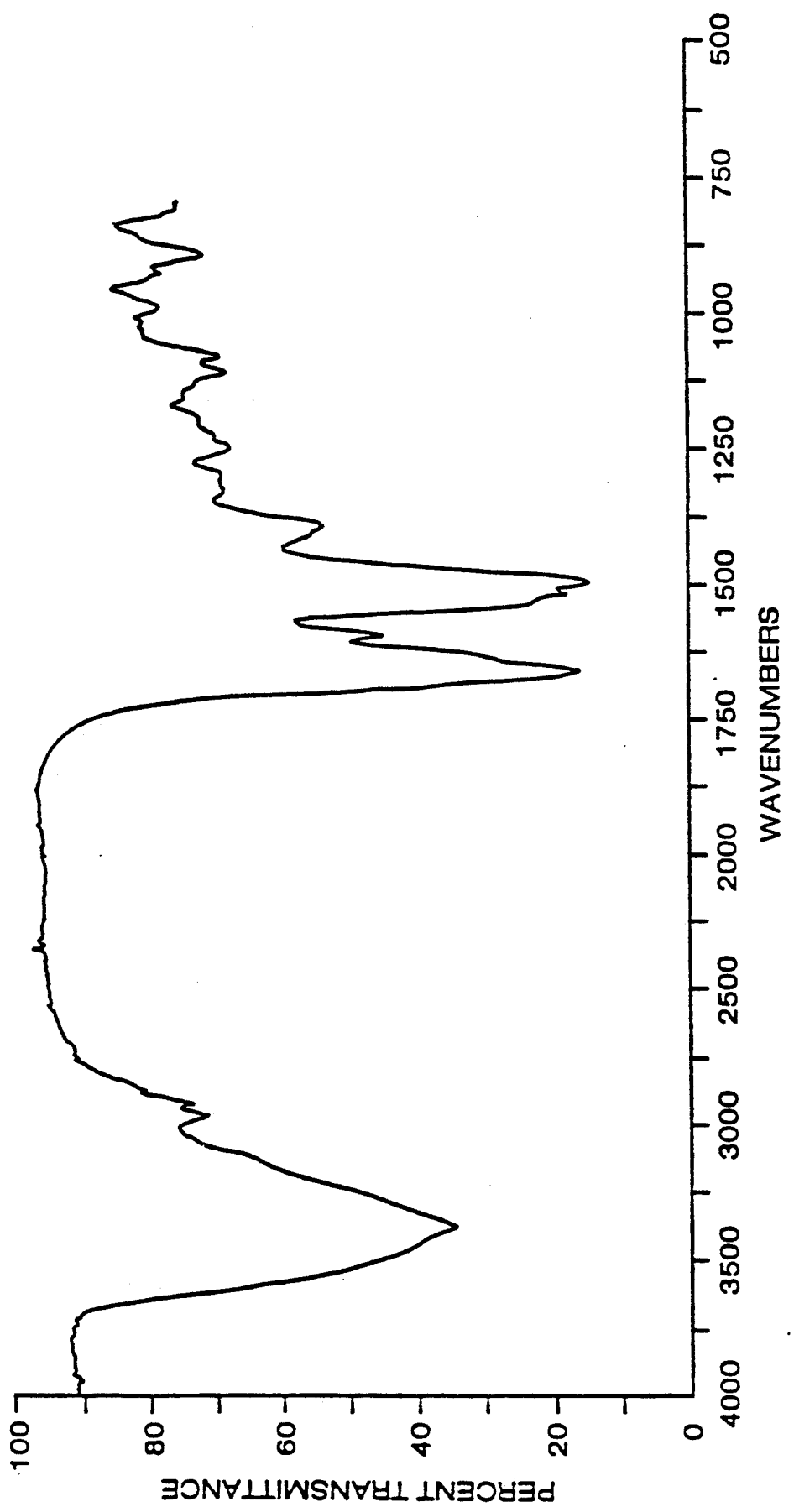
FIG. 1—A10255 Factor B.

The infrared absorption spectrum (KBr disc) is set forth in FIG. 1 of the accompanying drawings. The more significant absorption maxima observed in the spectrum are those at 3373, 2969, 2932, 2875, 1661, 1598, 1520, 1494, 1395, 1250, 1114, 1084, 996, 932, and 900 $cm^{-1}$:

The proton nuclear magnetic resonance spectrum of factor B was obtained in perdeuterated dimethylsulfoxide at 500 MHz and had the following signals:

| Resonance No. | Shift | Multiplicity |
| --- | --- | --- |
| 1 | 10.53 | S |
| 2 | 9.95 | S |
| 3 | 9.86 | S |
| 4 | 9.79 | S |
| 5 | 9.61 | S |
| 6 | 9.58 | S |
| 7 | 9.09 | S |
| 8 | 8.90 | T |
| 9 | 8.84 | D |
| 10 | 8.67 | S |
| 11 | 8.60 | S |
| 12 | 8.51 | S |
| 13 | 8.48 | D |
| 14 | 8.39 | S |
| 15 | 8.25 | D |
| 16 | 8.24 | S |
| 17 | 8.04 | D |
| 18 | 6.53* | S |
| 19 | 6.39 | T |
| 20 | 6.11 | S |
| 21 | 5.95 | S |
| 22 | 5.84 | S |
| 23 | 5.82 | S |
| 24 | 5.79 | S |
| 25 | 5.76+ | S |
| 26 | 5.68 | S |
| 27 | 5.64 | S |
| 28 | 5.44 | DQ |
| 29 | 5.16 | D |
| 30 | 4.80 | DD |
| 31 | 4.67 | DD |
| 32 | 4.63 | DD |
| 33 | 4.24 | BS |
| 34 | 2.21 | DQ |
| 35 | 1.62 | D |
| 36 | 1.11 | D |
| 37 | 1.01 | T |

*Doubly intense
+Triply intense

The $^{13}C$ nuclear magnetic resonance spectrum of factor B was obtained in perdeuterated dimethylsulfoxide at 125 MHz and had the following signals:

| Resonance No. | Shift | Multiplicity |
| --- | --- | --- |
| 1 | 172.88 | S |
| 2 | 169.17 | S |
| 3 | 168.87 | S |
| 4 | 164.90 | S |
| 5 | 163.67 | S |
| 6 | 163.07 | S |
| 7 | 162.84 | S |
| 8 | 162.68 | S |
| 9 | 162.61 | S |
| 10 | 161.57 | S |
| 11 | 160.32 | S |
| 12 | 160.17 | S |
| 13 | 160.01 | S |
| 14 | 159.46 | S |
| 15 | 158.96 | S |
| 16 | 158.10 | S |
| 17 | 149.39 | S |
| 18 | 149.37 | S |
| 19 | 148.79 | S |
| 20 | 142.05 | S |
| 21 | 146.88 | S |
| 22 | 142.05 | D |
| 23 | 141.32 | D |
| 24 | 140.68 | D |
| 25 | 139.23 | S |
| 26 | 136.33 | S |
| 27 | 136.29 | S |
| 28 | 136.14 | S |
| 29 | 135.26 | D |
| 30 | 134.23 | S |
| 31 | 133.82 | S |
| 32 | 133.28 | S |
| 33 | 130.21 | S |
| 34 | 129.07 | S |
| 35 | 127.22 | D |
| 36 | 125.94 | D |
| 37 | 124.98 | D |
| 38 | 122.36 | S |
| 39 | 121.47 | D |
| 40 | 110.92 | T |
| 41 | 110.49 | T |
| 42 | 109.98 | T |
| 43 | 109.46 | T |
| 44 | 106.23 | T |
| 45 | 104.73 | T |
| 46 | 67.37 | D |
| 47 | 57.94 | D |
| 48 | 46.33 | D |
| 49 | 40.24 | T |
| 50 | 20.74 | T |
| 51 | 20.67 | Q |
| 52 | 12.93 | Q |
| 53 | 12.93 | Q |

S = singlet; D = doublet; T = triplet; Q = quartet

It has been determined that A10255 factor B has the following structure.

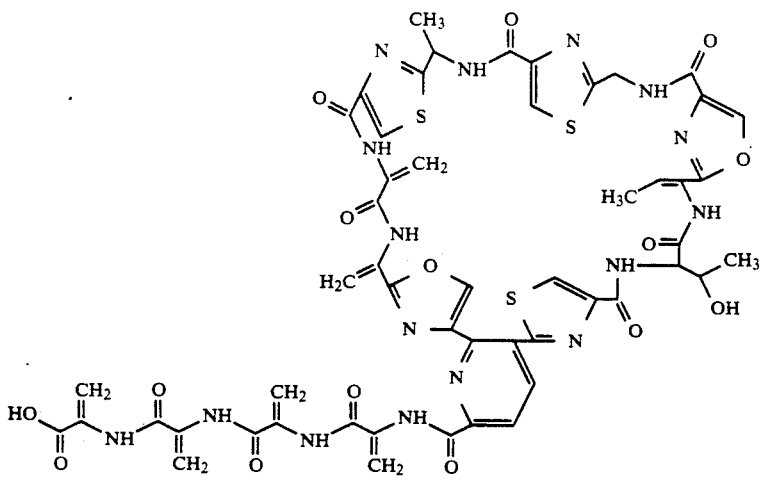

The remaining factors are believed to be similar in structure.

A10255 Factor C

A10255 factor C is a non-crystalline white to light-yellow powder which is soluble in dimethylsulfoxide, dimethylformamide, pyridine, 1:1 (v:v) methylene chloride/methanol, and 4:1 (v:v) tetrahydrofuran:water.

Elemental analysis of factor C indicates the following approximate percentage composition (average): carbon, 49.18%; hydrogen, 3.86%; nitrogen, 17.89%; oxygen, 18.28%; and sulfur, 6.46%.

The apparent molecular weight of A10255 factor C was determined by fast atom bombardment mass spectrometry to be approximately 1174 daltons. Using CsI as reference standard, exact mass was determined to be 1175.35 (M+H).

Electrometric titration of A10255 factor C in 66% aqueous dimethylformamide (initial pH, 7.29) indicated the presence of two titratable groups with pKa values of 2.9 (uncertain) and 12.0. Amino acid analysis of the factor C (after hydrolysis with 6N hydrochloric acid) indicated the presence of ammonia (7,429 mmoles/mg) and threonine (758 mmoles/mg). The analysis also evinced a large, unidentified peak coming before the position for the histidine peak.

The ultraviolet absorption spectrum for factor C obtained in neutral, acidic, and basic methanol demonstrated $\lambda_{max}$ of 245 nm $\epsilon = 63,000$).

Figure 2:
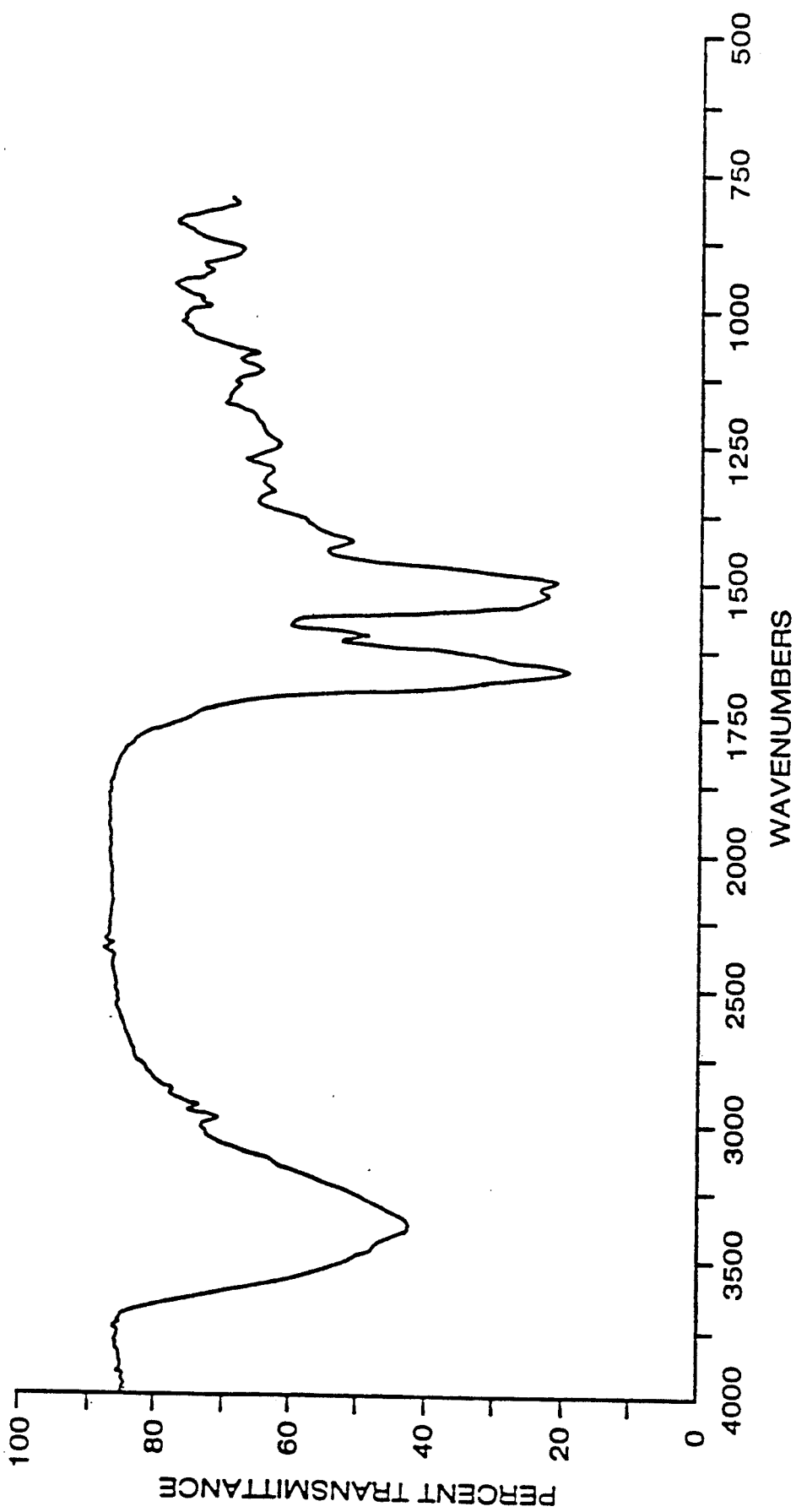
FIG. 2—A10255 Factor C.

The infrared absorption spectrum (KBr disc) is reproduced as FIG. 2 of the accompanying drawings. The more significant absorption maxima observed in the spectrum occur at 3375, 2973, 2932, 2876, 1661, 1597, 1494, 1427, 1345, 1305, 1249, 1111, 1083, 984, 933, and 894 cm$^{-1}$:

The proton nuclear magnetic resonance spectrum of factor C was obtained in perdeuterated dimethylsulfoxide at 360 MHz and had the following signals: $\delta$ 10.51, 10.08, 9.84, 9.57, 9.10, 8.88, 8.03, 7.94, 7.53, 5.15 (all of the foregoing are exchangeable with D$_2$O), 8.67, 8.59, 8.51, 8.49, 8.38, 8.25, 8.24, 6.57, 6.52, 6.38, 6.11, 5.91, 5.78, 5.74, 5.70, 5.65, 5.63, 5.44, 5.15, 4.79, 4.67, 4.63, 4.23, 2.21, 1.62, 1.11, and 1.01.

A10255 Factor E

A10255 factor E is a non-crystalline white to light-yellow powder which is soluble in dimethylsulfoxide, dimethylformamide, pyridine, chloroform/methanol mixtures, and 4:1 (v:v) tetrahydrofuran:water.

Elemental analysis of factor E indicates the following approximate percentage composition (average): carbon, 48.03%; hydrogen, 3.91%; nitrogen, 15.76%; oxygen, 17.09%; and sulfur, 5.63%.

The apparent molecular weight of A10255 factor E was determined by fast atom bombardment mass spectrometry to be approximately 1258 daltons. The exact mass of factor E was determined to be 1259.55 (M+H) using CsI as reference standard.

Electrometric titration of A10255 factor E in 66% aqueous dimethylformamide indicates the presence of three titratable groups with pKa values of 4.85, 11.1, and 13.2. Amino acid analysis of the factor E (after hydrolysis with 6N hydrochloric acid) indicates the presence of ammonia (8,580 mmoles/mg) and threonine (716 mmoles/mg). The analysis also evinced a large, unidentified peak coming before the position of the histidine peak.

The ultraviolet absorption spectrum for factor E obtained in neutral, acidic, and basic methanol demonstrated a $\lambda_{max}$ of 245 nm $\epsilon = 77,000$).

Figure 3:
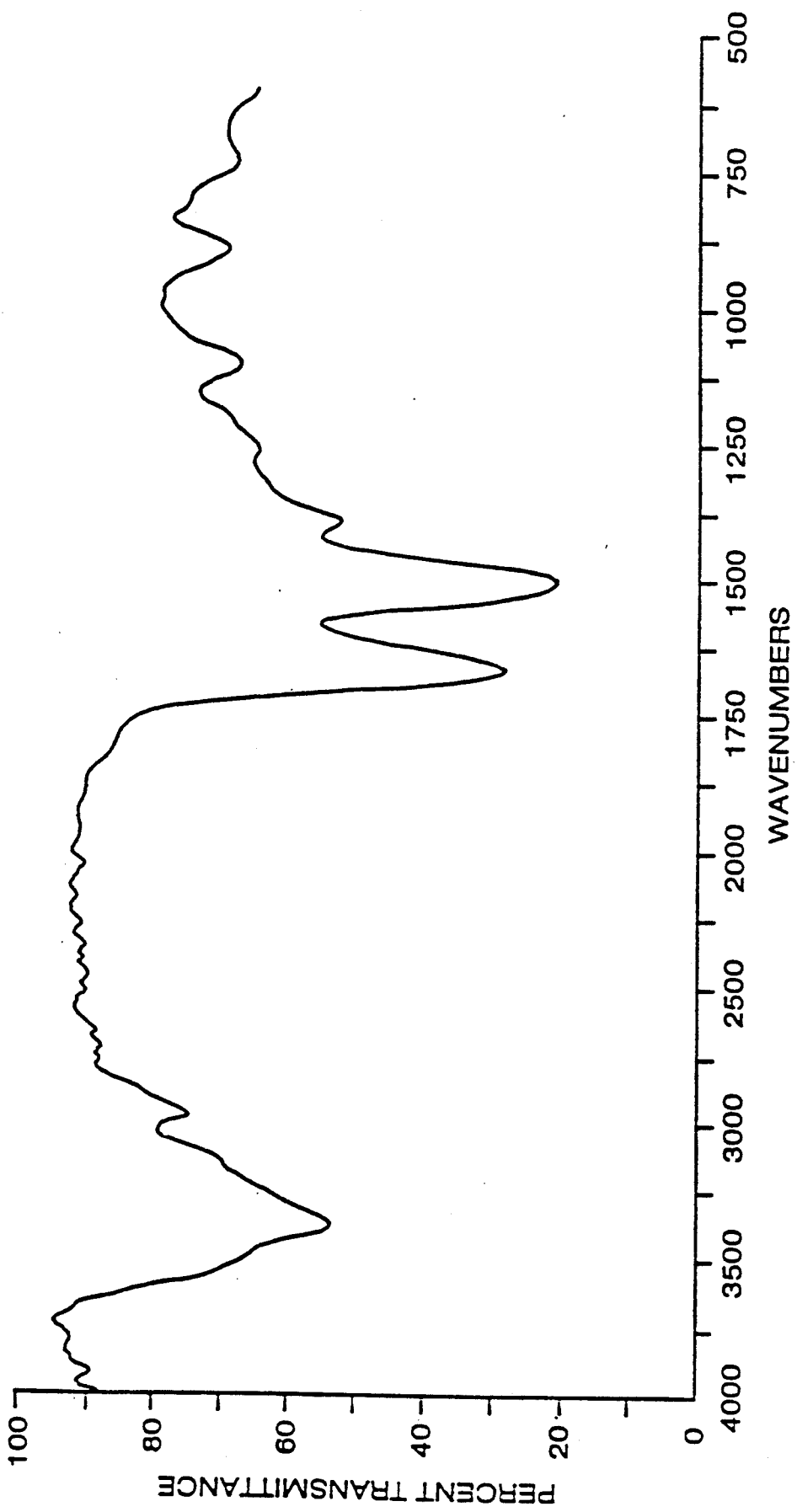
FIG. 3—A10255 Factor E.

The infrared absorption spectrum (KBr disc) is reproduced in FIG. 3 of the accompanying drawings. The more significant absorption maxima observed in the spectrum occur at 3367, 3361, 2966, 1664, 1501, 1389, 1254, 1102, and 889 cm$^{-1}$.

The proton nuclear magnetic resonance spectrum of factor E was obtained in perdeuterated dimethylsulfoxide at 270 MHz and had the following signals: $\delta$ 10.54, 10.00, 9.94, 9.81, 9.60, 9.56, 9.45, 8.89, 8.84, 8.66, 8.59, 8.50, 8.47, 8.39, 8.25, 8.22, 8.10, 6.53, 6.50, 6.24, 5.95, 5.86, 5.84, 5.77, 5.64, 5.55, 5.52, 5.44, 5.10, 4.80, 4.66, 4.64, 4.22, 2.78, 1.60, 1.11, and 1.00.

A10255 Factor F

A10255 factor F is a white to light-yellow non-crystalline powder which is soluble in dimethylsulfoxide, dimethylformamide, pyridine, 1:1 (v:v) methyl chloride/methanol, and 4:1 (v:v) tetrahydrofuran:water.

Elemental analysis of factor F indicates the following approximate percentage composition (average): carbon, 49.65%; hydrogen, 4.23%; nitrogen, 17.11%; oxygen, 22.08%; and sulfur, 7.78%.

The apparent molecular weight of A10255 factor F was determined by first atom bombardment mass spectrometry to be approximately 1188 daltons.

Electrometric titration of A10255 factor F in 66% aqueous dimethylformamide (starting pH of 7.08) indicates the presence of a titratable group with a pKa value of 12.5.

Amino acid analysis of the factor F (after hydrolysis with 6N hydrochloric acid) indicates the presence of ammonia (7,226 mmoles/mg) and threonine (735 mmoles/mg). The analysis also evinced a large, unidentified peak coming before the position of the histidine peak.

The ultraviolet absorption spectrum for factor F obtained in neutral, acidic, and basic methanol demonstrated a $\lambda_{max}$ of 245 nm ($\epsilon=71,500$).

Figure 4:
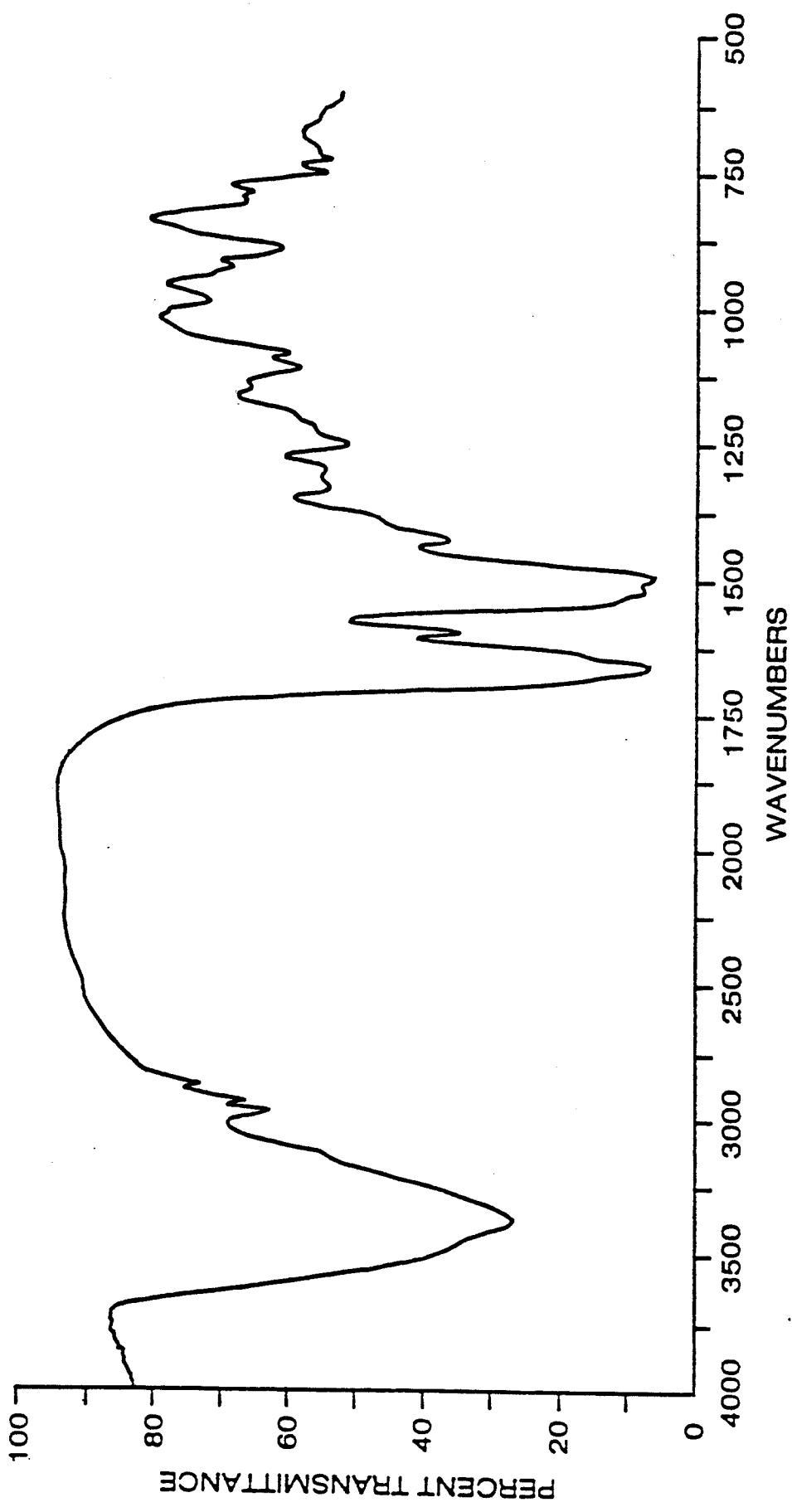
FIG. 4—A10255 Factor F.

The infrared absorption spectrum (KBr disc) is reproduced as FIG. 4 of the accompanying drawings. The more significant absorption maxima observed in the spectrum occur at 3369, 2943, 2907, 2846., 1663, 1588, 1519, 1493, 1425, 1337, 1288, 1251, 1151, 1110, 1083, 995, 927, 890, 807, 776, and 751 cm$^{-1}$.

The proton nuclear magnetic resonance spectrum of factor F was obtained in perdeuterated dimethylsulfoxide at 360 MHz and had the following signals: $\delta$ 10.51, 10.17, 9.88, 9.77, 9.54, 9.10, 8.90, 8.88, 8.66, 8.59, 8.51, 8.49, 8.38, 8.25, 8.24, 8.06, 7.94, 7.53, 6.56, 6.51, 6.27, 6.23, 6.12, 6.12, 5.96, 5.77, 5.76, 5.71, 5.71, 5.64, 5.62, 5.47, 5.14, 4.77, 4.65, 4.62, 4.20, 2.77, 2.48, 2.48, 1.58, 1.08, 0.98, and 0.98.

A10255 Factor G

A10255 factor G is a non-crystalline white to light-yellow powder which is soluble in dimethylsulfoxide, dimethylformamide, pyridine, chloroform/methanol mixtures and 4:1 (v:v) tetrahydrofuran:water.

Elemental analysis of factor G indicates the following approximate percentage composition:

| Elemental Analysis: | |
|---|---|
| | Found (%) |
| C | 51.46 |
| H | 3.82 |
| N | 17.62 |
| O | 19.38 |
| S | 7.03 |
| | 99.31% |

The ultraviolet absorption spectrum for factor G in neutral ethanol demonstrated a $\lambda_{max}=247$ nm ($\lambda=72,200$); acidic solution, $\lambda_{max}=247$ nm ($\epsilon=73,400$); and basic solution, $\lambda_{max}=211$ nm ($\epsilon=27,200$).

Figure 5:
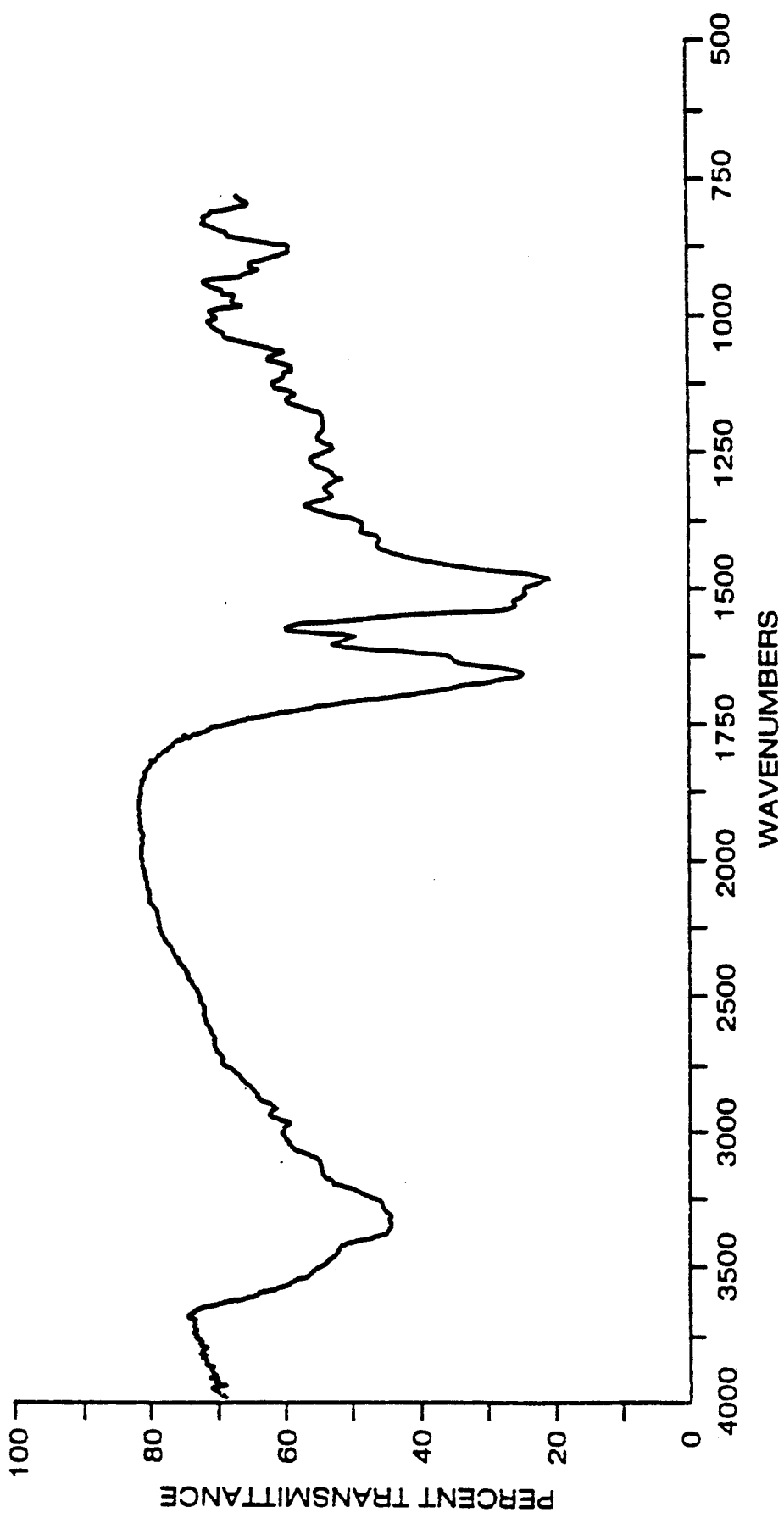
FIG. 5—A10255 Factor G.

The infrared absorption spectrum of factor G is reproduced as FIG. 5 of the accompanying drawings. The more significant absorption maxima observed in the spectrum occur at 3389, 3117, 2981, 2928, 1663, 1643, 1600, 1538, 1517, and 1495 cm$^{-1}$.

The $^1$H nuclear magnetic resonance spectrum of factor G was obtained in perdeuterated dimethylsulfoxide at 500 MHz and had the following signals:

| Resonance No. | Shift | Multiplicity |
|---|---|---|
| 1 | 10.53 | S |
| 2 | 9.95 | S |
| 3 | 9.83 | S |
| 4 | 9.79 | S |
| 5 | 9.59* | BS |
| 6 | 9.09 | S |
| 7 | 8.89 | T |
| 8 | 8.84 | D |
| 9 | 8.68 | S |
| 10 | 8.60 | S |
| 11 | 8.51 | S |
| 12 | 8.48 | D |
| 13 | 8.39 | S |
| 14 | 8.24 | S |
| 15 | 8.24 | D |
| 16 | 8.04 | D |
| 17 | 6.53* | S |
| 18 | 6.47 | Q |
| 19 | 6.10 | S |
| 20 | 5.95 | S |
| 21 | 5.84 | S |
| 22 | 5.81 | S |
| 23 | 5.80 | S |
| 24 | 5.78 | S |
| 25 | 5.76* | S |
| 26 | 5.68 | S |
| 27 | 5.64 | S |
| 28 | 5.44 | DQ |
| 29 | 5.16 | D |
| 30 | 4.75 | DD |
| 31 | 4.67 | DD |
| 32 | 4.63 | DD |
| 33 | 4.24 | BS |
| 34 | 1.77 | Q |
| 35 | 1.62 | Q |
| 36 | 1.11 | Q |

*Doubly intense
BS = broad singlet
DD = doublet of doublets
DQ = doublet of quartet The $^{13}$C Nuclear Magnetic Resonance Spectrum of factor G was obtained in perdeuterated dimethylsulfoxide at 125 MHz:

| Resonance No. | Shift | Multiplicity |
|---|---|---|
| 1 | 172.80 | S |
| 2 | 168.89 | S |
| 3 | 168.71 | S |
| 4 | 164.80 | S |
| 5 | 163.59 | S |
| 6 | 163.00 | S |
| 7 | 162.79 | S |
| 8 | 162.61 | S |
| 9 | 162.53 | S |
| 10 | 161.52 | S |
| 11 | 160.24 | S |
| 12 | 160.12 | S |
| 13 | 159.94 | S |
| 14 | 159.42 | S |
| 15 | 158.91 | S |
| 16 | 158.01 | S |
| 17 | 149.41 | S |
| 18 | 148.73 | S |
| 19 | 148.04 | S |
| 20 | 146.83 | S |
| 21 | 141.94 | D |
| 22 | 141.26 | D |
| 23 | 140.62 | D |
| 24 | 139.20 | S |
| 25 | 136.25 | S |
| 26 | 136.20 | S |
| 27 | 136.04 | S |
| 28 | 134.20 | S |
| 29 | 133.81 | S |
| 30 | 133.22 | S |
| 31 | 130.14 | S |
| 32 | 128.99 | D |
| 33 | 128.70 | S |
| 34 | 127.08 | D |
| 35 | 125.83 | D |
| 36 | 124.92 | D |
| 37 | 123.66 | S |
| 38 | 121.40 | D |
| 39 | 110.77 | T |
| 40 | 110.22 | T |
| 41 | 109.85 | T |
| 42 | 109.35 | T |

-continued

| Resonance No. | Shift | Multiplicity |
|---|---|---|
| 43 | 106.12 | T |
| 44 | 104.65 | T |
| 45 | 67.26 | D |
| 46 | 57.94 | D |
| 47 | 46.49 | D |
| 48 | 40.12 | Q |
| 49 | 20.60 | Q |
| 51 | 20.22 | Q |
| 52 | 13.41 | Q |

A10255G has been determined to have the following structure:

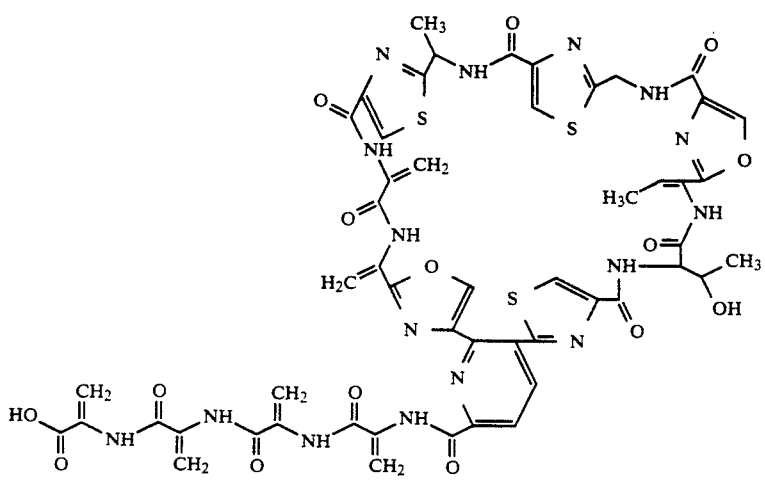

A10255 Factor H

A10255 factor H is a non-crystalline white to light-yellow powder which is soluble in dimethylsulfoxide, sulfoxide, dimethylformamide, pyridine, 1:1 (v:v) methylene chloride/methanol, and 4:1 (v:v) tetrahydrofuran:water. Elemental analysis of factor H indicates the following approximate percentage composition:

| Elemental Analysis: | |
|---|---|
| | Found (%) |
| C | 50.36 |
| H | 3.72 |
| N | 18.61 |
| O | 18.54 |
| S | 8.20 |
| | 99.43% |

The ultraviolet absorption spectrum for factor H in neutral ethanol demonstrated a $\lambda_{max}$ of 244 nm ($\epsilon=74,000$); acidic solution, $\lambda_{max}=245$ nm ($\epsilon=74,500$); and basic solution, $\lambda_{max}=211$ nm ($\epsilon=23,800$).

The $^{13}C$ nuclear magnetic resonance spectrum of A10255 factor H at 125 MHz in perdeuterated dimethylsulfoxide had the following signals:

| Resonance | Shift | Multiplicity |
|---|---|---|
| 1 | 172.92 | S |
| 2 | 168.92 | S |
| 3 | 168.86 | S |
| 4 | 165.14 | S |
| 5 | 163.63 | S |
| 6 | 163.03 | S |
| 7 | 162.65 | S |
| 8 | 162.33 | S |
| 9 | 161.52 | S |
| 10 | 160.30 | S |
| 11 | 160.14 | S |
| 12 | 159.99 | S |
| 13 | 159.45 | S |
| 14 | 158.94 | S |
| 15 | 158.09 | S |
| 16 | 149.43* | S |
| 17 | 148.78 | S |
| 18 | 148.03 | S |
| 19 | 146.90 | S |
| 20 | 142.07 | D |
| 21 | 141.30 | D |
| 22 | 140.68 | D |
| 23 | 139.21 | S |
| 24 | 136.96 | S |
| 25 | 136.10 | S |
| 26 | 134.67 | S |
| 27 | 134.07 | S |
| 28 | 133.80 | S |
| 29 | 130.27 | S |
| 30 | 129.03 | S |
| 31 | 128.78 | D |
| 32 | 127.24 | D |
| 33 | 125.94 | D |
| 34 | 124.99 | D |
| 35 | 123.71 | S |
| 36 | 121.50 | D |
| 37 | 111.76 | T |
| 38 | 110.45 | T |
| 39 | 106.11 | T |
| 40 | 104.67 | T |
| 41 | 104.44 | T |
| 42 | 67.39 | D |
| 43 | 57.95 | D |
| 44 | 46.54 | D |
| 45 | 40.22 | T |
| 46 | 20.66 | Q |
| 47 | 20.34 | Q |
| 48 | 13.52 | Q |

*Doubly intense

The $^1H$ nuclear magnetic resonance spectrum at 500 MHz in perdeuterated dimethylsulfoxide had the following signals:

| Resonance | Shift | Multiplicity |
|---|---|---|
| 1 | 10.51 | S |
| 2 | 10.08 | S |
| 3 | 9.81 | S |
| 4 | 9.79 | S |

| Resonance | Shift | Multiplicity |
|---|---|---|
| 5 | 9.57 | S |
| 6 | 9.10 | S |
| 7 | 8.86 | T |
| 8 | 8.83 | D |
| 9 | 8.68 | S |
| 10 | 8.60 | D |
| 11 | 8.51 | S |
| 12 | 8.50 | D |
| 13 | 8.39 | S |
| 14 | 8.25 | D |
| 15 | 8.24 | S |
| 16 | 8.03 | D |
| 17 | 7.94 | S |
| 18 | 7.53 | S |
| 19 | 6.56 | S |
| 20 | 6.53 | S |
| 21 | 6.48 | Q |
| 22 | 6.12 | S |
| 23 | 5.96 | S |
| 24 | 5.80 | S |
| 25 | 5.78 | S |
| 26 | 5.74 | S |
| 27 | 5.72 | S |
| 28 | 5.65 | S |
| 29 | 5.64 | S |
| 30 | 5.44 | DQ |
| 31 | 5.15 | D |
| 32 | 4.80 | DD |
| 33 | 4.68 | DD |
| 34 | 4.63 | DD |
| 35 | 4.24 | BS |
| 36 | 1.78 | D |
| 37 | 1.62 | D |
| 38 | 1.10 | D |

Figure 6:
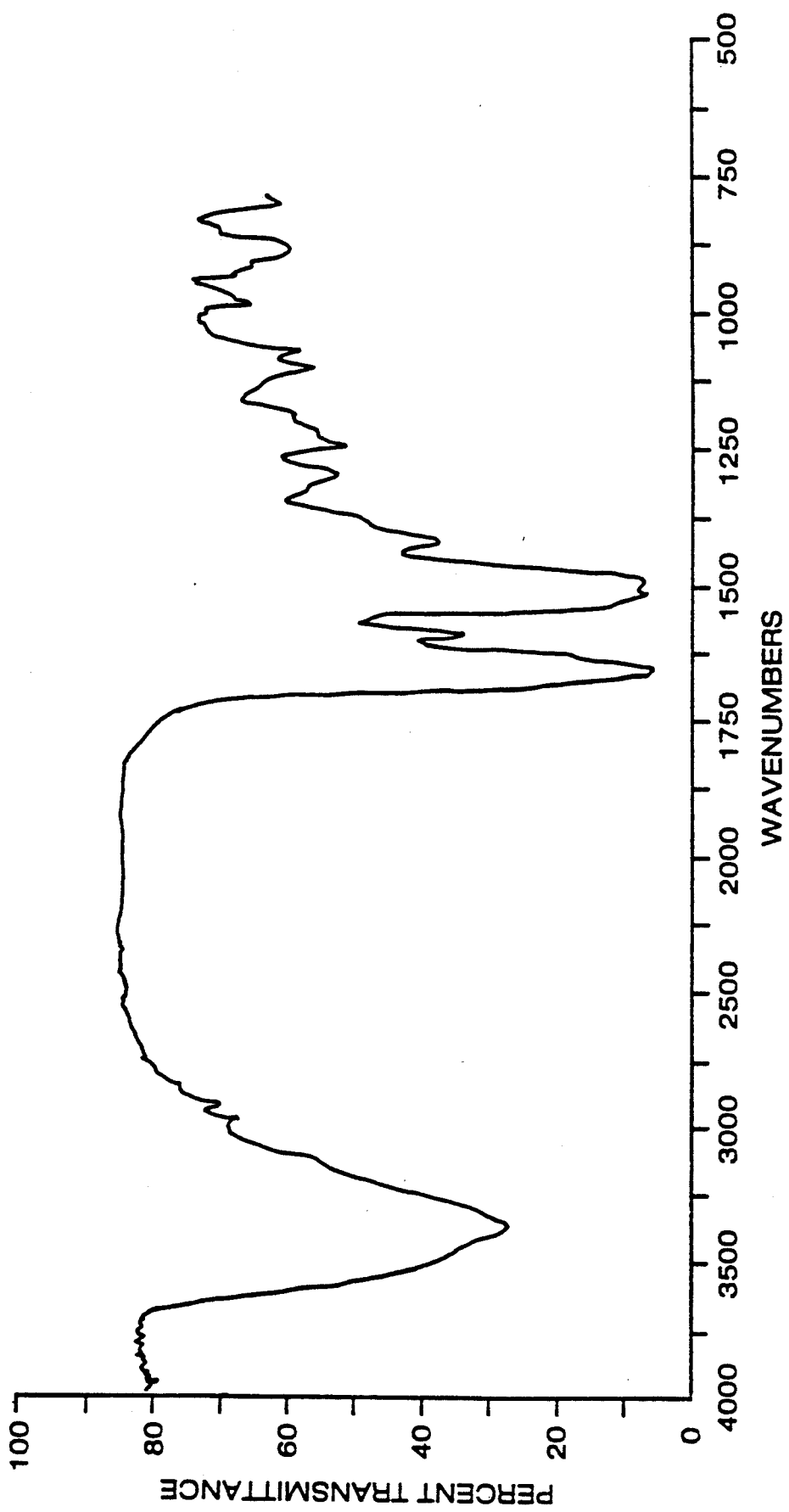
FIG. 6—A10255 Factor H.

The infrared spectrum (KBr disc) for A10255 factor H is set forth in FIG. 6 of the accompanying drawings. The more significant absorption maxima observed in the spectrum occur at 3390, 3139, 2982, 2932, 1662, 1598, 1531, 1520, 1496, and 1428 cm$^{-1}$.

The molecular weight of A10255 factor H was determined by fast atom bombardment mass spectrometry to be approximately 1160; the exact mass was determined to be 1161.32 (M+H) using CsI as reference standard.

A10255 Factor J

A10255 factor J is a non-crystalline white to light-yellow powder which is soluble in dimethylsulfoxide, dimethylformamide, pyridine, 1:1 (v:v) methylene chloride/methanol, and 4:1 (v:v) tetrahydrofuran/water.

Elemental analysis of factor J indicates the following approximate percentage composition:

| | Found % |
|---|---|
| C | 49.08 |
| H | 3.74 |
| N | 17.64 |
| O | 20.75 |
| S | 9.23 |

The ultraviolet absorption spectrum for factor H in neutral ethanol demonstrated a $\lambda_{max}$ of 246 nm ($\epsilon$=62,000).

The $^1$H nuclear magnetic resonance spectrum of A10255 factor J at 270 MHz in perdeuterated dimethylsulfoxide had the following signals:

| Position | Shift | Multiplicity |
|---|---|---|
| 1 | 10.69 | S |
| 2 | 9.86 | S |
| 3 | 9.80 | S |
| 4 | 9.58 | S |
| 5 | 8.87 | T |
| 6 | 8.84 | D |
| 7 | 8.60 | S |
| 8 | 8.58 | S |
| 9 | 8.53 | S |
| 10 | 8.51 | S |
| 11 | 8.49 | D |
| 12 | 8.39 | S |
| 13 | 8.25 | D |
| 14 | 8.23 | S |
| 15 | 8.15 | S |
| 16 | 8.04 | D |
| 17 | 7.65 | S |
| 18 | 6.55 | S |
| 19 | 6.53 | S |
| 20 | 6.48 | Q |
| 21 | 5.82 | S |
| 22 | 5.80 | S |
| 23 | 5.66 | S |
| 24 | 5.44 | M |
| 25 | 5.16 | D |
| 26 | 4.79 | DD |
| 27 | 4.68 | DD |
| 28 | 4.63 | DD |
| 29 | 4.25 | BM |
| 30 | 1.78 | D |
| 31 | 1.62 | D |
| 32 | 1.12 | D |

Figure 7:
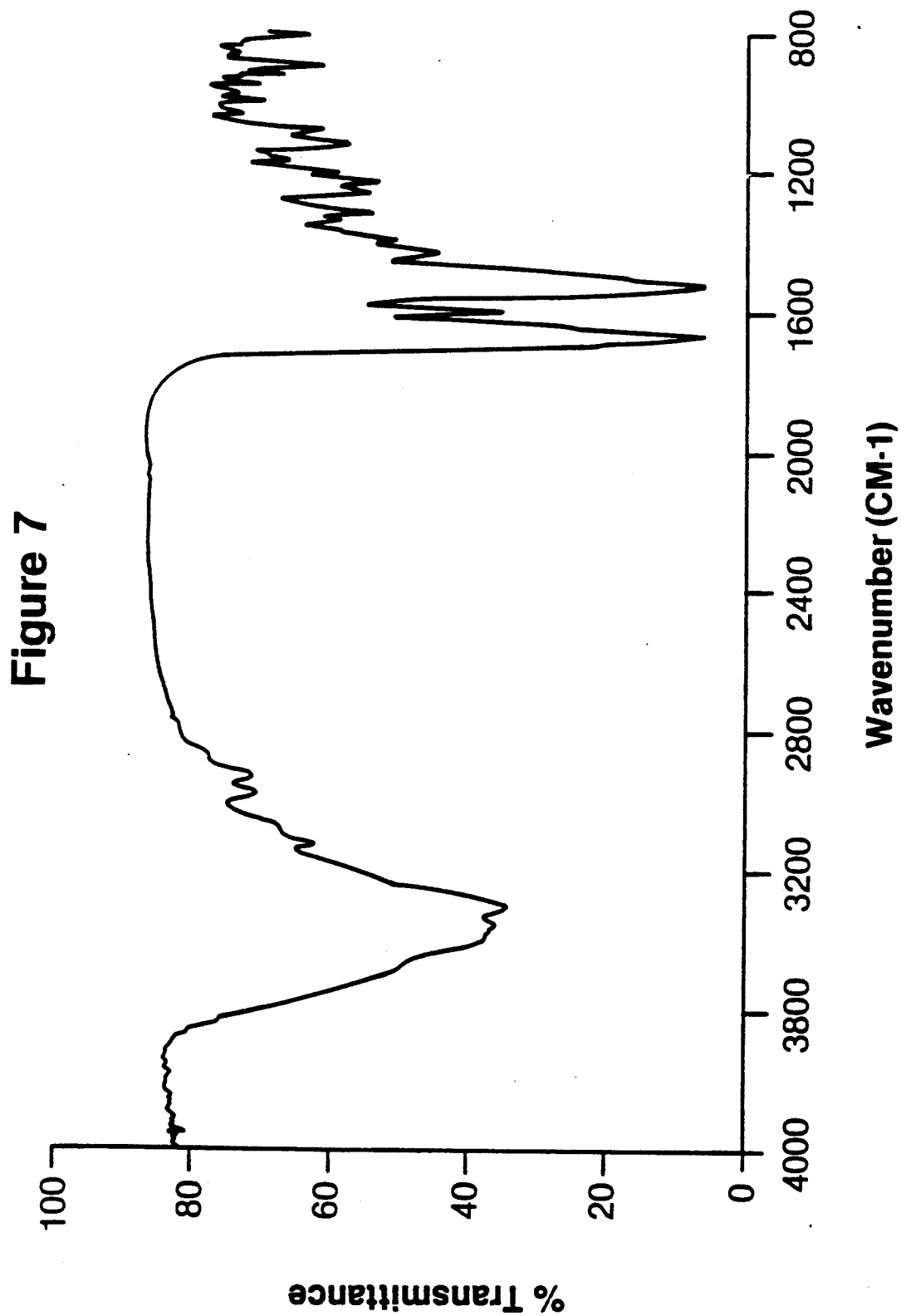
FIG. 7—A10255 Factor J.

The infrared spectrum (KBr disc) for A10255 factor J is set forth in FIG. 7 of the accompanying drawings. The more significant absorption maxima observed in the spectrum occur at 3354, 3298, 3123, 2971, 2928, 1666, 1597, 1523, and 1424 cm$^{-1}$.

The molecular weight of A10255 factor J was determined by fast atom bombardment mass spectrometry to be approximately 1023 (m+1); the exact mass was determined to be 1023.2085.

The $^{13}$C nuclear magnetic resonance spectrum of A10255 factor J at 67.9 MHz in perdeuterated dimethylsulfoxide had the following signals:

| Position | Shift | Multiplicity |
|---|---|---|
| 1 | 172.80 | S |
| 2 | 168.86 | S |
| 3 | 168.68 | S |
| 4 | 164.93 | S |
| 5 | 163.52 | S |
| 6 | 162.58 | S |
| 7 | 161.10 | S |
| 8 | 160.20 | S |
| 9 | 160.07 | S |
| 10 | 159.92 | S |
| 11 | 158.86 | S |
| 12 | 159.38 | S |
| 13 | 158.02 | S |
| 14 | 149.63 | S |
| 15 | 149.39 | S |
| 16 | 148.70 | S |
| 17 | 148.00 | S |
| 18 | 146.70 | S |
| 19 | 141.89 | D |
| 20 | 141.17 | D |
| 21 | 140.25 | D |
| 22 | 139.14 | S |
| 23 | 136.06 | S |
| 24 | 133.76 | S |
| 25 | 130.09 | S |
| 26 | 128.96 | S |
| 27 | 128.63 | D |
| 28 | 127.06 | D |
| 29 | 125.78 | D |
| 30 | 124.87 | D |

-continued

| Position | Shift | Multiplicity |
|---|---|---|
| 31 | 123.65 | S |
| 32 | 121.28 | D |
| 33 | 110.25 | T |
| 34 | 104.62 | T |
| 35 | 103.00 | T |
| 36 | 67.23 | D |
| 37 | 57.92 | D |
| 38 | 46.50 | D |
| 39 | 40.16 | T |
| 40 | 30.41 | D |
| 41 | 20.59 | Q |
| 42 | 20.21 | Q |
| 43 | 13.39 | Q |

A10255 factor J has been determined to have the following structure:

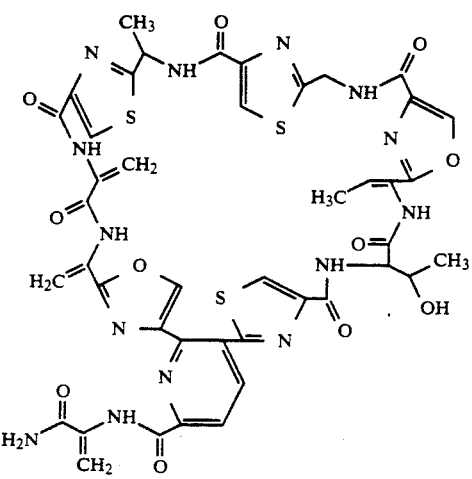

The term "pharmaceutically-acceptable salts" includes alkali and alkaline earth metal salts of the compounds of the present invention, for example, lithium, sodium, potassium and calcium, as well as acid addition salts such as those which are formed between the compounds of the present invention and acids such as hydrochloric, hydrobromic, sulfuric and phosphoric acids.

The A10255-producing parent strain S. gardneri NRRL 15537, also identified originally as A10255.1, has been classified as such by taxonomic studies carried out as described by the following paragraphs.

Taxonomy of the A10255.1 Strain

Taxonomic studies of the A10255.1 strain were carried out by Mr. Frederick P. Mertz of the Lilly Research Laboratories. Based on these studies, the organism is classified as a new strain of Streptomyces gardneri (Waksman 1942) Waksman 1961 ATCC 23911. This classification is based on an examination of published descriptions of this species [R. E. Buchanan, and N. E. Gibbons (eds.), "Bergey's Manual of Determinative Bacteriology", 8th Edition, The Williams and Wilkins Co., Baltimore, 1974; E. B. Shirling and D. Gottlieb., "Cooperative Description of Type Cultures of Streptomyces", Int. J. Syst. Bacteriol. 18(4):279-392 (1968); and S. A. Waksman, "The Actinomycetes Vol. II", The Williams and Wilkins Co., Baltimore, 1961] and simultaneous laboratory comparsions.

The methods recommended by the International Streptomyces Project (ISP) for the characterization of Streptomyces species [E. B. Shirling and D. Gottlieb, "Methods for Characterization of Streptomyces Species", Int. J. Syst. Bacteriol. 16(3), 313-340 (1966)] were followed along with certain supplementary tests D. J. Blazevic and G. M. Ederer, "Principles of Biochemical Tests in Diagnostic Microbiology", John Wiley and Sons, Inc., New York, 1975].

Carbon utilization was determined on ISP No. 9 basal medium to which filter-sterilized carbon sources were added to equal a final concentration of 1.0 percent. Plates were incubated at 30° C. and read after 14 days.

Melanoid pigment production (chromogenicity) was determined with ISP No. 1 (tryptone-yeast extract broth), ISP No. 6 (peptone-yeast extract iron agar), ISP No. 7 (tyrosine agar), and modified ISP No. 7 which has tyrosine removed.

Starch hydrolysis was determined by testing for the presence of starch with iodine on ISP No. 4 (inorganic salts-starch agar) plates (see Blazevic and Ederer, supra).

Morphology was studied using an optical light microscope. A scanning electron microscope (SEM) was used to study the spore surface ornamentation.

Sodium chloride tolerance was measured by adding sodium chloride to ISP No. 2 agar to equal the concentration desired.

ICSS-NBS Centroid Color Charts, standard sample No. 2106 (National Bureau of Standards, 1958, U.S. Department of Commerce, Washington, D.C.) and the Color Harmony Manual (4th ed., Color Standards Department, Container Corporation of America, Chicago, Ill., 1958) were used to assign color names.

The cell wall sugars were determined with the procedure of M. P. Lechevalier, "Identification of Aerobic Actinomycetes of Clinical Importance," J. Lab. Clin. Med., 71, 934-944 (1968). The isomers of diaminopimelic acid (DAP) were established by the chromatographic methods set forth in B. Becker, M. P. Lechevalier, R. E. Gordon, and H. A. Lechevalier, "Rapid Differentiation between Nocardia and Streptomyces by Paper Chromatography of Whole-cell Hydrolysates", Appl. Microbiol 11, 421-423 (1964).

Cultural Characteristics

A10255.1 is characterized by limited vegetative and very poorly developed aerial mycelia. The aerial mycelia has a spore mass color in the white (W) to gray (GY) color series. The nearest matching color tab in the Tresner and Backus system [Color Harmony Manual, supra, and E. J. Backus and H. D. Tresner, "System of Color Wheels for Streptomyces Taxonomy, Appl. Microbiol., 11, 335-338 (1956)] for the white color series is b oyster white and in the gray color series is d light gray. This cultural feature is best observed on glycerol asparagine agar (ISP No. 5). Aerial mycelia is so poorly developed on most media that a color determination is very difficult.

The reverse side of this culture has no distinctive pigments. The color of the reverse side is orange-yellow to yellow-brown and the color is unaffected by pH. The only soluble pigment produced is a light brown pigment on tyrosine agar (ISP No. 7) and tomato paste oatmeal agar (TPO) and a light-orange pigment produced on Glycerol-Glycine agar. When plated for variability, this culture was stable and homogeneous.

Cultural characteristics of the A10255.1 strain and S. gardneri ATCC 23911 are set forth below in Table 1.

TABLE 1

Cultural Characteristics of A10255.1 and S. gardneri ATCC 23911

| Agar | | A10255.1 | S. gardneri |
|---|---|---|---|
| ISP No. 2 | [a]G: | Fair | Fair |
| | [b]R: | 72.d.OY | 72.d.OY |
| | [c]Am: | Poor: b White (edges only) d light Gray | Poor: d light Gray (edges only) |
| | Sp: | None | None |
| ISP No. 3 | G: | Trace to Fair | Trace |
| | R: | 70.1.OY | — |
| | Am: | Trace b White (edges only) | None — |
| | Sp: | None | None |
| Calcium Malate | G: | Fair | Fair |
| | R: | 79.1.gy.yBr | 93.yGray |
| | Am: | None → trace | Trace: b White |
| | SP: | None | None |
| Czapek's | G: | Fair | Abundant |
| | R: | 93.yGray | 79.1.gy. yBr |
| | Am: | Poor: b White | Abundant: b White |
| | Sp: | None | None |
| Glucose Asparagine | G: | Fair | Fair |
| | R: | 72.d.OY | 90.gy.Y |
| | Am: | Poor: b White | None: — |
| | Sp: | None | None |
| ISP No. 7 | G: | Good | Good |
| | R: | 54.brO | 77.m.yBr |
| | Am: | Poor: b White | Poor: b White |
| | Sp: | light-brown | very light brown |
| Glycerol Glycine | G: | Fair | Fair - (wrinkled surface) |
| | R: | 53.m.O (no pH change) | 90. gy.Y |
| | Am: | None | None |
| | Sp: | light-orange | None |
| TPO | G: | Good | Good |
| | R: | 54. brO (no pH change) | 72.d.OY |
| | Am: | Poor: (edges only) 3ca pale orange yellow | Poor: (edges only) d light Gray |
| | Sp: | light orange-brown | None |
| ISP No. 4 | G: | Fair | Fair |
| | R: | 71.m.OY | 91.d.gy.Y |
| | Am: | Poor: b White | Poor: d light Gray |
| | Sp: | None | None |
| ISP No. 5 | G: | Fair | Fair |
| | R: | 70.1.OY | 90.gy.Y |
| | Am: | Fair: b White to d 1.Gray | Trace: — |
| | Sp: | None | None |

[a]G = Growth; R = Reverse; Am = Aerial Mycelia; Sp = Soluble pigment.
[b]Coding of reverse colors follows the ICSS-NBS System, Supra.
[c]Coding of aerial color follows the Color Harmony Manual, Supra.

Morphological Characteristics

Culture A10255.1 produces a poorly developed non-fragmenting aerial mycelium which is monopodially branched. Sporophores are arranged as straight and flexuous branches. No spirals, sclerotia, sporangia, or motile spores were observed. A10255.1 is placed in the Rectus-flexibilus (RF) section of Pridham et al. [T. G. Pridham et al., "A Guide for the Classification of Streptomyces According to Selected Groups", Appl. Microbiol., 6, 52-79 (1957)].

The same morphology is observed on all media where aerial mycelia could be observed. Mature spore chains generally contain from 10 to 50 spores per chain. The spore shape is cylindrical. The spore size ranges from 0.9-1.0 $\mu$M in length and 0.5-0.6 $\mu$M in width. The average size is 1.6×0.6 $\mu$M. The spore surface ornamentation is smooth.

Physiological Characteristics

Whole cell hydrolysates contain LL-diaminopimelic acid with no meso isomer present. Sugars present in whole cell hydrolysates were glucose, mannose, and ribose. These characteristics represent a Type I cell wall and a NC, or no characteristic, sugar pattern [M. P. Lechevalier, supra]. This combination of major cell wall constituents is indicative of the genus Streptomyces [M. P. Lechevalier, supra, and R. E. Buchanan and N. E. Gibbons (eds)., supra].

The carbon utilization pattern for A10255.1 is as follows: L-arabinose, D-fructose, D-galactose, D-glucose, i-inositol, raffinose, and D-xylose are utilized for growth. D-mannitol, L-rhamnose, salicin and sucrose do not support growth. Table 2 below compares the carbon utilization patterns observed for A10255.1 and S. gardneri ATCC 23911.

TABLE 2

Utilization of Carbon Compounds by A10255.1 S. gardneri ATCC 23911

| Carbon Source | A10255.1 | S. gardneri |
|---|---|---|
| No carbon | −[a] | − |
| L-arabinose | +[b] | + |
| D-fructose | + | + |
| D-galactose | + | + |
| D-glucose | + | + |
| i-inositol | + | − |
| D-mannitol | − | − |
| raffinose | + | + |
| L-rhamnose | − | + |
| salicin | − | − |
| sucrose | − | + |
| D-xylose | + | + |

−[a] = no utilization
+[b] = utilization

Culture A10255.1 hydrolyzed starch and partially hydrolyzed skim milk, produced catalase, liquified gelatin, and reduced nitrates to nitrites.

A10255.1 will tolerate up to 6 percent sodium chloride and will grow at temperatures ranging from 4° to 40° C.

Melanoid pigments are produced when A10255.1 is grown in tryptone-yeast extract broth (ISP No. 1) and on slants of peptone-yeast extract iron agar (ISP No. 6). No melanoid pigments were produced on slants of tyrosine agar (ISP No. 7).

Species Determination

Using the cultural, morphological, and physiological characteristics of A10255.1, comparison was made with the published descriptions of similar species. Four species of Streptomyces were selected to examine in simultaneous laboratory comparison: *Streptomyces aureofasciculus*[a], *Streptomyces aureomonopodiales*[a], *Streptomyces flavochromogenes*[b], *Streptomyces gardneri*[c].
[a]E. B. Shirling and D. Gottlieb, "Cooperative Description of Type Cultures of Streptomyces", Int. J. Syst. Bacteriol., 19(4), 375-390 (1969).
[b]E. B. Shirling and D. Gottlieb, "Cooperative Description of Type Cultures of Streptomyces", Int. J. Syst. Bacteriol. 22(4), 265-394 (1972).
[c]E. B. Shirling and D. Gottlieb, "Cooperative Description of Type Cultures of Streptomyces", Int. J. Syst. Bacteriol. 18(4), 279-392 (1968).

Laboratory comparisons indicated significant differences with S. aureofasciculus and S. flavochromogenes, and good agreement with S. aureomonopodiales and S. gardneri. However, as S. aureomonopodiales is not in the Approved List of Bacterial Names, it was removed from consideration.

A10255.1 is quite similar to S. gardneri in cultural, morphological, and physiological characteristics. The predominate cultural feature that distinguishes both strains is the very poor formation of aerial hyphae on most media. S. gardneri is described in the literature as belonging in the Gray (GY) series. However, in the original description by Waksman [S. A. Waksman, supra], and in laboratory comparisons with A10255.1, it produced white (W) and gray (GY) aerial hyphae. The reverse color of both cultures is almost identical. Both cultures possess a Rectus-flexibilus (RF) morphology, smooth spore surface ornamentation, cylindrical spore shape, and chains of 10–50 spores.

Catalase production, liquefaction of gelatin, melanoid pigment production, reduction of nitrate, and hydrolysis of milk and starch were the same for both strains.

Differences between A10255.1 and *S. gardneri* are minimal. *S. gardneri* had less tolerance to sodium chloride and a lower temperature range than A10255.1. The utilization of L-rhamnose, sucrose, and inability to utilize i-inositol distinguish *S. gardneri* from A10255.1. These similarities and differences are summarized below.

| Comparison Between A10255.1 and *Streptomyces gardneri* | |
|---|---|
| Similarities | Differences |
| Aerial spore mass color (W) | Carbon utilization |
| Catalase positive | Sodium chloride tolerance |
| Cell wall hydrolysates (LL-DAP) | Temperature range |
| Distinctive pigments absent | |
| Gelatin liquefaction | |
| Morphology (RF) | |
| Nitrate reduction | |
| Partial milk hydrolysis | |
| Reverse pigmentation | |
| Soluble pigments absent | |
| Spore chain length | |
| Spore shape | |
| Spore surface ornamentation (Sm) | |
| Starch hydrolysis | |

The similarities and differences between the two cultures are set forth below in detail in Table 3:

TABLE 3

| Comparison of A10255.1 and *S. gardneri* ATCC 23911 | | |
|---|---|---|
| Characteristics | A10255.1 | *S. gardneri* |
| Aerial spore mass color | (W) | (W) |
| Carbon utilization pattern | | |
| i-inositol | + | − |
| L-rhamnose | − | + |
| sucrose | − | + |
| Catalase | + | + |
| Cell wall type | I | I |
| Distinctive pigments | − | − |
| Gelatin liquefaction | + | + |
| Melanoid pigment production | | |
| ISP No. 1 | + | + |
| ISP No. 6 | + | + |
| ISP No. 7 | − | − |
| Morphology | (RF) | (RF) |
| NaCl tolerance - % | 6 | 4 |
| Nitrate reduction | + | + |
| Reverse color | YBr | YBr |
| Skim milk hydrolysis | partial | partial |
| Soluble pigments | − | − |
| Spore chain length | 10–50 | 10–50 |
| Spore shape | cylindrical | cylindrical |
| Spore surface | smooth | smooth |
| Starch hydrolysis | + | + |
| Temperature range - °C. | 4–40 | 4–37 |

The results of the above comparisons indicate that A10255.1 is very similar to *S. gardneri*. Therefore culture A10255.1 is classified as a strain of *Streptomyces gardneri* (Wakesman, 1942) Waksman 1961, ATCC 23911. *S. gardneri* is recognized in the Approved List of Bacterial Names [V. B. D. Skerman et al., "Approved Lists of Bacterial Names", *Int. J. Syst. Bacteriol.*, 30 (1), 225–420 (1980)] and consequently is a validly published species.

It should be mentioned that Kurylowicz et al. [W. Kurylowicz, A. Paszkiewicz, W. Woznicka, and W. Kurzatkowski, "Numerical Taxonomy of Streptomyces", Polish Medical Publishers, 1975], when classifying Streptomyces, in both the Wroclaw dentrite of similarity and the Overall Similarity Method numerical methods place *S. aureomonopodiales* and *S. gardneri* in the same cluster. A dendrogram based on this study relates these two strains at a percentage similarity of 94. This similarity suggests that a distinction in species is not justified.

The *Streptomyces gardneri* culture described above has been deposited and made a part of the stock culture collection of the Northern Regional Research Division, U.S. Department of Agriculture, Agricultural Research Service, Peoria, Ill. 61604. Upon issuance of the instant specification, the culture will be made available to the public from this branch of the Department of Agriculture under the number NRRL 15537.

Description of the A10255.10 Strain (NRRL 18260)

The A10255.10 strain NRRL 18260 is derived from the parent strain A10255.1, NRRL 15537, by a series of sequential treatments with NTG (N-nitrosoguanidine).

Production of the Antibiotic Factors and Their Biological Activity

The A10255 antibiotic complex can be produced by culturing the previously undescribed microorganism *Streptomyces gardneri*, NRRL 15537 or strain NRRL 18260, or an A10255-producing mutant thereof, in a culture medium containing assimilable sources of carbon, nitrogen, and inorganic salts, under submerged aerobic fermentation conditions until the A10255 antibiotic complex is produced, and preferably until a substantial level of antibiotic activity is produced. Most of the antibiotic activity is generally found associated with the mycelia, while minor amounts of antibiotic activity are found in the broth. The A10255 complex is most readily separated from the fermentation mixture by removal of the mycelia (the biomass) by filtration. The broth is generally discarded. The antibiotic complex is then isolated from the mycelia.

The parent strain NRRL 15537 produces factor B as the most abundant factor. The mutant strain NRRL 18260 produces B and G as the most abundant factors. The remaining factors C, E, F, H, and J have thus far been produced in only minor amounts with either strain.

The mycelia are extracted with polar solvents (such as 4:1 acetone:water), concentrated, again extracted with an organic solvent (ethyl acetate, for example), and the resultant solutions are concentrated to precipitate the A10255 complex.

The A10255 complex can be used without further purification and mixed directly into animal feed or animal feed premix. Alternatively, the A10255 antibiotic complex can be further purified and separated into its individual factors by well-known chromatographic techniques such as thin layer chromatography, column chromatography, and especially various high performance liquid chromatography procedures. Some specific procedures for isolating the individual factors are discussed in the Experimental Section.

A number of different media may be used with NRRL 15537 or NRRL 18260 to produce the A10255 complex. For economy in production, optimal yield, and ease of product isolation, however, certain culture media are preferred. These media should contain assimilable sources of carbon, nitrogen, and inorganic salts. Suitable carbon sources include glucose, starch, maltose, fructose, and glycerol. Optimum levels of carbon sources are from about 2 to about 5 percent by weight.

Preferred nitrogen sources include acid digest of soybeans, acid or enzymatic digests of casein, ammonium salts, nitrate salts, glycine, alanine, serine, asparagine, and glutamine.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, ferrous, chloride, carbonate, phosphate, sulfate, nitrate, and like ions.

Although small quantities of the A10255 antibiotic may be obtained by shake-flask culture, submerged aerobic fermentation in stirred bioreactors is a preferred method for producing substantial quantities of the A10255 antibiotic. For stirred bioreactor fermentation, it is preferable to use a vegetative inoculum. The vegetative inoculum is prepared by inoculating a small volume of culture medium with the spore form, or mycelial fragments, to obtain a fresh, actively growing culture of the organism. The vegetative inoculum is then transferred to a larger bioreactor where, after a suitable incubation time, the A10255 antibiotic is produced in optimal yield.

The A10255-producing organisms produce the A10255 complex over a temperature range of from about 23° to about 37° C. Optimum production of A10255 antibiotic complex appears to occur at a temperature of about 30° to about 32° C.

As is customary in aerobic submerged culture processes, sterile air is dispersed through the culture medium. For efficient growth of organism, the volume of air used in tank production is in the range of from about 0.1 to about 0.5 volumes of air per volume of culture medium per minute (v/v/m), with from about 150 to about 300 RPM agitation. An optimum rate in a 165-liter vessel containing 115 liters of fermentation medium is about 0.125 v/v/m, with agitation provided by an impeller rotating at about 300 RPM.

The fermentation generally produces antibiotic activity after about 20 hours. Peak antibiotic production occurs at >160 hours fermentation time.

Production of the A10255 antibiotic can be monitored during the fermentation by either agar diffusion using *Bacillus subtilis* ATCC 6633, by a turbidimetric method using *Staphylococcus aureus* ATCC 9114, or by HPLC.

Another method for producing the A10255 antibiotic complex and its individual factors is by culturing the A10255.2 strain. The strain is also a strain of *Streptomyces gardneri* ((Waksman 1942) Waksman 1961 ATCC 23911) and has the deposit number NRRL 15922. The culturing techniques for the A10255.2 strain are similar to the instant A10255.1 strain and are discussed in L. D. Boeck, O. Godfrey and K. H. Michel, U. S. application Ser. No. 06/941,473, filed Dec. 15, 1986, herein incorporated by reference.

The A10255 complex and individual factors are antimicrobial agents and are especially active against gram-positive microorganisms, as illustrated by the following in vitro and in vivo test data. In the following Table 4 is presented the minimum inhibitory concentration, (MIC, in micrograms/milliliters), for the factors against a sampling of pathogenic gram-positive and gram-negative bacteria. The MIC values were obtained by the standard agar dilution test method.

TABLE 4

Activity of A10255 Compounds vs. Pathogenic Microorganisms

| Test Organism | MIC (mcg/ml) | | | |
|---|---|---|---|---|
| | B | C | E | F |
| Staphylococcus aureus X1.1 | 0.125 | 0.03 | 0.25 | 0.03 |
| Staphylococcus aureus V41 | 0.5 | 0.125 | 0.25 | 0.06 |
| Staphylococcus aureus X400 | 0.5 | 0.125 | 0.5 | 0.06 |
| Staphylococcus aureus S13E | 0.5 | 0.06 | 0.125 | 0.03 |
| Staphylococcus epidermidis 270 | 0.25 | 0.03 | 0.25 | 0.03 |
| Staphylococcus epidermidis 222 | 0.5 | 0.125 | 0.5 | 0.06 |
| Streptococcus pyogenes C203 | 0.125 | 0.06 | 0.125 | 0.03 |
| Streptococcus pneumoniae Park I | 0.125 | 0.015 | 0.125 | 0.015 |
| Streptococcus group D X66 | 0.25 | 0.06 | 0.25 | 0.06 |
| Streptococcus group D 2041 | 0.5 | 0.125 | 0.25 | 0.125 |
| Hemophilus influenzae C.L. (sens.) | >128 | 64 | >128 | >128 |
| Hemophilus influenzae 76 (res.) | >128 | 16 | 16 | 128 |

The A10255 compounds also demonstrate excellent antimicrobial activity against a number of *Clostridium difficile* strains. In particular, in standard agar dilution tests the A10255 complex and factors B, C, E, and F exhibited MIC's of less than or equal to 0.03 microgram/milliliter. By comparison, in the same tests used for the complex and factors B and C, the antibiotic vancomycin exhibited an MIC of 2 or 4 microgram/milliliter.

The A10255 complex and factor C were tested against several Bacteroides species and demonstrated excellent antimicrobial activity. The results of this agar-dilution test are set forth below in Table 5.

TABLE 5

Activity of A10255 Compounds vs. Select Bacteroides Species Strains

| Test Organism | MIC (mcg/ml) | |
|---|---|---|
| B. fragilis strains | A10255 Complex | Factor C |
| 1877 | 0.5 | 0.5 |
| 103 | 0.5 | 0.5 |
| 104 | 0.06 | 0.06 |
| 106 | 0.06 | 0.06 |
| 107 | 1.0 | 1.0 |
| 108 | 1.0 | 1.0 |
| 110 | 0.5 | 0.5 |
| 111 | 1.0 | 1.0 |
| 112 | 1.0 | 1.0 |
| 113 | 1.0 | 1.0 |
| 1451 | 0.25 | 0.25 |
| 1470 | 1.0 | 1.0 |
| 2 | 0.5 | 0.5 |
| 9 | 1.0 | 1.0 |
| 9032 | 1.0 | 1.0 |
| B. corrodens 1874 | 0.5 | 0.5 |

TABLE 5-continued

Activity of A10255 Compounds vs. Select Bacteroides Species Strains

| Test Organism B. fragilis strains | MIC (mcg/ml) | |
|---|---|---|
| | A10255 Complex | Factor C |
| B. vulgatis 1563 | 0.25 | 0.25 |
| B. thetaiotaomicron 1438 | 0.5 | 0.5 |
| B. thetaiotaomicron 1900A | 0.5 | 0.5 |

The A110255 complex and the individual factors have demonstrated antimicrobial activity against a wide variety of anaerobic microorganisms. The antimicrobial activity is set forth below in Table 6. The results set forth in the Table are MIC values from a standard agar dilution test.

TABLE 6

Activity of A10255 Compounds vs. Anaerobic Bacteria

| Test Organism | MIC (mcg/ml) | | | | |
|---|---|---|---|---|---|
| | Complex | B | C | E | F |
| Clostridium difficile 2994 | 0.125 | ≦0.06 | 0.125 | ≦0.03 | ≦0.03 |
| Clostridium perfringens 81 | ≦0.06 | ≦0.06 | ≦0.06 | ≦0.03 | ≦0.03 |
| Clostridium septicum 1128 | ≦0.06 | ≦0.06 | ≦0.06 | ≦0.03 | ≦0.03 |
| Eubacterium aerofaciens 1235 | ≦0.06 | ≦0.06 | ≦0.06 | ≦0.03 | ≦0.03 |
| Peptococcus asaccharolyticus 1302 | 1.0 | ≦0.06 | 1.0 | ≦0.03 | 0.06 |
| Peptococcus prevoti 1281 | ≦0.06 | ≦0.06 | ≦0.06 | 0.125 | 0.125 |
| Peptostreptococcus anaerobius 1428 | ≦0.06 | 2 | ≦0.06 | 2 | 1.0 |
| Peptococcus intermedius 1264 | 1.0 | >32 | 1.0 | 0.5 | 0.25 |
| Propionibacterium acnes 79 | 0.125 | >32 | 0.125 | 0.5 | 0.125 |
| Bacteroides fragilis 111 | 1.0 | >32 | 1.0 | 4 | 1.0 |
| Bacteroides fragilis 1877 | 2 | >32 | 2 | 4 | 1.0 |
| Bacteroides fragilis 1936B | 0.5 | >32 | 0.5 | 4 | 1.0 |
| Bacteroides thetaiotaomicron 1438 | 0.5 | 0.5 | 0.5 | 1.0 | 0.25 |
| Bacteroides malaninogenicus 1856/28 | 1.0 | >32 | 1.0 | 4 | 4 |
| Bacteroides melaninogenicus 2736 | 0.5 | 4 | 0.5 | 0.5 | 0.125 |
| Bacteroides vulgatis 1211 | 0.5 | 4 | 0.5 | 1.0 | 0.25 |
| Bacteroides corrodens 1874 | 0.25 | >32 | 0.25 | 2 | 0.5 |
| Fusobacterium symbiosum 1470 | ≦0.06 | ≦0.06 | <0.06 | ≦0.03 | ≦0.03 |
| Fusobacterium necrophorum 6054A | ≦0.06 | ≦0.06 | <0.06 | ≦0.03 | ≦0.03 |

The A10255 complex and factor B demonstrated an LD$_{50}$ of greater than 300 mg/kg×1 and greater than 75 mg/kg×1, respectively. The results were obtained by intraperitoneal injection in mice.

The A10255 antibiotics are growth-promoting agents in economically important warm-blooded animals such as poultry, swine, and cattle. In chickens, the A10255 complex improved weight gains and feed efficiency. Table 7 summarizes the results of two tests in which the complex was fed ad libitum to 7-day old chicks for fourteen days in battery testing (ten pens of seven chicks per treatment). The growth-performance data from the chicks treated with the complex was compared to that of an equal number of replicates of a contemporary control treatment.

The growth-enhancing effect in poultry is illustrated by the following test data obtained with chickens.

TABLE 7

Growth Promotant Activity of A10255 Complex in Chickens

| Diet | Treatment | (g/ton) | Weight Gain | | Feed/Gain | |
|---|---|---|---|---|---|---|
| | | | Weight g | % Improvement[1] | Ratio | % Improvement |
| Corn | Control | — | 331 | — | 1.724 | — |
| | A10255 | 5 | 358 | 8.2 | 1.688 | 2.1 |
| | Complex | 20 | 350 | 5.7 | 1.714 | 0.6 |
| Rye | Control | — | 313 | — | 1.974 | — |
| | A10255 | 5 | 373 | 19.2 | 1.718 | 13.0 |
| | Complex | 20 | 358 | 14.4 | 1.817 | 7.9 |

[1] $\frac{\text{Treatment mean}}{\text{Control mean}} \times 100 = \%$ improvement In order to promote the growth of chickens, the A10255 complex or the individual factors thereof should be administered with the chicken's feed at rates of from about 0.5 to about 50 grams of A10255 complex or individual factor per ton of chicken feed. Most beneficial results are observed when the A10255 complex or individual factor is administered at rates of from about 5 to about 20 grams of A10255 complex or factor per ton of chicken feed.

A further aspect of this invention provides feed compositions for increasing feed utilization efficiency and promoting growth in poultry. The feed composition comprises chicken feed and an effective amount of the A10255 complex, A10255 factor B, A10255 factor C, A10255 factor E, A10255 factor F, A10255 factor G, A10255 factor H, or A10255 factor J, or any combination of factors thereof, or a pharmaceutically-acceptable salt thereof. An "effective amount" of the complex or the individual factors or salt form thereof is from about 0.5 to about 50 grams per ton, and preferably from about 5 to about 20 grams per ton, of chicken feed. The chicken feed used in the feed composition can be any standard ration for chickens.

Formulation of the feed compositions is accomplished by mixing procedures well known in the veterinary pharmaceutical art.

A preferred feed composition comprises an effective amount of the A10255 complex and chicken feed.

The A10255 complex exhibits growth promotant and enhanced feed efficiency activity in weanling pigs as shown by the activity data set forth below in Table 8. Table 8 summarizes the results of nine trials employing the complex. In these trials the pigs had an average beginning weight of 24 lbs and finished the study at an average weight of 53 lbs. The pigs were housed 4 to a pen in an environmentally controlled nursery facility and were fed ad libitum an 18% protein corn-soy diet. All studies spanned 35 days, used two to three experimental units per treatment, and an average of fourteen animals per treatment.

In Table 8, the figures in parenthesis indicate the change in percent from the control group. A negative percentage change in the "Feed/Gain" column indicates an improvement in the Feed/Gain (feed efficiency) of the pigs fed the A10255 complex.

TABLE 8

Effect of A10255 Complex on the Weanling Pigs

| Expt. No. | Ave. Init. Pig Wt. (lbs) | Total No. Pigs/Treatment | Compound | Level (ppm) | Average Daily Gain (lbs) | Average Daily Feed (lbs) | Feed/Grain |
|---|---|---|---|---|---|---|---|
| 1 | 26.0 | 15 | Control | 0 | 1.031 | 2.208 | 2.141 |
|   | 26.0 | 15 | A10255 | 20 | 1.154(11.9) | 2.408(9.1) | 2.094(−2.2) |
| 2 | 26.0 | 12 | Control | 0 | 1.299 | 2.748 | 2.129 |
|   | 26.0 | 12 | A10255 | 20 | 1.250(−3.8) | 2.569(−6.5) | 2.054(−3.5) |
| 3 | 24.0 | 17 | Control | 0 | 1.004 | 2.099 | 2.094 |
|   | 24.0 | 17 | A10255 | 20 | 1.073(6.9) | 2.215(5.5) | 2.061(−1.6) |
| 4 | 28.0 | 14 | Control | 0 | 1.155 | 2.341 | 2.020 |
|   | 28.0 | 14 | A10255 | 20 | 1.188(2.9) | 2.383(1.8) | 2.004(−0.8) |
| 5 | 29.0 | 11 | Control | 0 | 1.206 | 2.470 | 2.048 |
|   | 28.0 | 9 | A10255 | 20 | 1.229(1.9) | 2.548(3.2) | 2.074(1.3) |
| 6 | 21.0 | 11 | Control | 0 | 1.096 | 2.149 | 1.963 |
|   | 20.0 | 12 | A10255 | 20 | 1.061(−3.2) | 2.162(0.6) | 2.032(3.5) |
| 7 | 23.0 | 14 | Control | 0 | 1.139 | 2.297 | 2.012 |
|   | 24.0 | 14 | A10255 | 40 | 1.233(8.3) | 2.759(20.1) | 2.233(11.0) |
| 8 | 19.0 | 14 | Control | 0 | 1.029 | 1.990 | 1.922 |
|   | 19.0 | 13 | A10255 | 40 | 1.057(2.7) | 2.002(0.6) | 1.884(−2.0) |
| 9 | 22.0 | 17 | Control | 0 | 1.013 | 2.136 | 2.118 |
|   | 22.0 | 16 | A10255 | 40 | 1.050(3.7) | 2.182(2.2) | 2.077(−1.9) |

Another aspect of the invention provides feed compositions for increasing feed utilization efficiency and promoting growth in weanling pigs. The feed comcompositions comprise swine feed and an effective amount of either the A10255 complex, A10255 factor B, A10255 factor C, A10255 factor E, A10255 factor F, A10255 factor G, A10255 factor H, A10255 factor J, or any combination of factors thereof, or a pharmaceutically-acceptable salt thereof.

The term "effective amount" in the feed composition for weanling pigs means approximately 20 to approximately 40 parts per million of the A10255 complex or individual factor per unit of whole feed. The feed used for the weanling pig composition is any of the normal feed rations used for weanling pigs. The feed composition may be formulated by any of the methods well known in the veterinary pharmaceutical art.

A preferred feed composition for weanling pigs comprises swine feed and an effective amount of the A10255 complex or a pharmaceutically-acceptable salt thereof.

The A10255 complex and the individual factors thereof also improve feed-utilization efficiency in ruminants which have a developed rumen function. The increase in efficiency caused by the A10255 antibiotics can be monitored by observing the production and concentration of propionate compounds in the rumen using the method described by James R. Beck and Joseph A. Yahner, U.S. Pat. No. 4,333,923, issued Jun. 8, 1982, herein incorporated by reference. Table 9 shows the ratio of volatile-fatty-acid (VFA) production in A10255 complex-treated flasks to production in control flasks in this test obtained from the method of Beck and Yahner.

TABLE 9

Effect of A10255 Complex on Ruminant Feed-Utilization Efficiency[1]

| Dosage mcg/mL | Propionate | Acetate | Butyrate | Total VFA mM/L |
|---|---|---|---|---|
| 5 | 1.623 | 0.903 | 0.538 | 1.03 |
| 1 | 1.406 | 0.965 | 0.604 | 1.02 |

[1]Ratio of production rates (moles/d) in treated flasks to production rates in control flasks.

The A10255 complex and the individual factors thereof are typically effective in increasing propionate and, thereby, the efficiency of feed utilization when administered to ruminants orally.

Further, as a natural consequence of this method of increasing feed utilization efficiency in ruminants by virtue of increased propionate production, one is also provided with means to control lactic acidosis and ketosis in ruminants.

The following Table 10 summarizes data demonstrating the effects of the A10255 complex on the growth and feed utilization of cattle. The study was conducted for a period of 79 days on three groups of animals.

TABLE 10

Effect of A10255 Complex on the Growth of Beef Cattle

| Group | A10255[a] Dose | Wt Gain[b] | Response | Feed Conversion | Response |
|---|---|---|---|---|---|
| 1[c] | 0 | 2.76 |  | 6.94 |  |
| 2[d] | 275 | 2.88 | (+4%) | 5.94 | 14% |
| 3[e] | 550 | 2.74 | (−1%) | 5.79 | 17% |

[a]mg/Head/day
[b]per day
[c]9 animals
[d]10 animals
[e]9 animals

Another aspect of this invention provides a method for increasing the feed utilization efficiency of cattle, which comprises administering to cattle an effective amount of A10255 complex, or an effective amount of an A10255 factor or a pharmaceutically-acceptable salt thereof. A preferred method comprises administering to cattle an effective amount of the A10255 complex.

According to the method provided herein for promoting growth in cattle, the animals are administered orally an effective amount of the A10255 complex or a factor thereof. The term "effective amount" refers to from about 0.05 mg/kg/day to about 5.0 mg/kg/day. Preferable rates of oral administration are from about 0.1 mg/kg/day to about 3.0 mg/kg/day. The antibiotic complex or factor may be administered orally with the cattle's feed; however, it can be administered in other ways, for example, drenches, boluses, or capsules. Mixing the A10255 compound with the cattle's feed is the preferred route of administration. Formulation of these various dosage forms is accomplished by methods well known in the veterinary pharmaceutical arts.

A further aspect of the invention provides a feed composition for increasing the feed utilization of cattle. The feed composition comprises cattle feed and an effective amount of the A10255 complex or an A10255 factor or a pharmaceutically-acceptable salt thereof. A preferred feed composition for cattle comprises cattle feed and an effective amount of the A10255 complex. The most highly preferred feed composition for cattle comprises the cattle feed and an effective amount of either A10255 factor B or A10255 factor G or a salt thereof. The individual A10255 factors B, C, E, F, G, H, and J appear to be roughly minimally bioequivalent.

In the above feed compositions for cattle, the term "effective amount" is as defined above for the method for enhancing feed utilization in cattle. The cattle feed used in conjunction with the feed composition can be any conventional feed ration for cattle.

As a further aspect of the method of feed utilization in cattle and sheep, the compounds of the present invention are useful in controlling lactic acidosis. In particular, the A10255 complex is useful in alleviating acidosis in cattle and sheep by shortening the duration of the condition following onset. The treated animals are thus restored to a healthy condition in a shorter time than untreated animals.

The following experiment illustrates the effectiveness of the A10255 complex in diminishing rumen lactic acid accumulation in sheep switched abruptly from roughage to concentrate diets:

Eighteen 45 kg rumen-cannulated wethers were used to evaluate the effect of compound A10255 (A) in moderating rumen pH and lactic acid levels. Animals adapted to a 65% concentrate ration were randomly allotted to 5 treatment groups (see table immediately below). On days 1, 2, 3 and 4 of the experiment, animals were fed alfalfa hay, and A or Monensin (M) administered intraruminally. On day 5, A and M were administered, and the animals were fasted. On day 6, rumen contents were sampled for A or M and 675 g of cornmeal administered intraruminally, and animals were refed a 65% concentrate ration. Additional rumen samples were taken also at 3, 6, 9, 12 and 24 hours postchallenge. A afforded good protection from acidosis at each time observed; 12-hour sample data are presented in the table. Rumen pH, total lactic acid and TVFA for control animals were different ($P<0.05$) than for A- or M-treated animals. Lactic acid and TVFA concentrations decreased and increased, respectively, ($P<0.01$) as A increased; pH increased with A ($P<0.01$) but dropped off at higher doses ($P<0.05$).

| Ruminal Observations; Day 6, 12-hr Sample | | | | |
|---|---|---|---|---|
| Treatment Group | Number Animals | Rumen pH | Ruminal Lactic Acid, mM/l | Ruminal TVFA, mM/l |
| Control | 4 | 4.45 | 104.7 | 10.9 |
| A, 15 mg/d | 4 | 5.26 | 47.5 | 86.1 |
| A, 30 mg/d | 4 | 5.51 | 19.7 | 89.8 |
| A, 60 mg/d | 7 | 5.40 | 19.6 | 102.6 |
| M, 60 mg/d | 3 | 5.02 | 61.3 | 43.6 |

The following experiment was conducted to show the effect of the A10255 complex on ruminal pH, organic acid levels, glucose levels and osmotic pressure and to assess the effective level of the A10255 complex:

MATERIALS AND METHODS

Animals and Diets

Four ruminally-fistulated steers were used in the trial. Three steers, one with rumen cannula and two with rumen and duodenal cannulae were used as donor animals. All animals were fed the 50% concentrate diet (50 C) composed of 20% dry rolled corn, 60% corn silage and 20% alfalfa hay. For two days of each period during the trial, the test animals were fed the 95% concentrate diet (95 C) composed of 47.5% dry rolled wheat, 47.5% dry rolled corn and 5% alfalfa hay.

Preliminary Experiment

A baseline experiment was conducted to determine the level of grain to be used to produce a measurable acidosis.

During the first day of the experiment, 20 liters of rumen contents from each test animal were replaced with the same volume of rumen fluid from the donor animals. The steers were fed the 50 C twice daily for 4 days. On day 5, the steers were only fed in the morning half of their daily consumption. On day 6, the steers were offered the 95 C and allowed to eat all they can in 4 hours. Any feed left after 4 hours was put in the rumen via the cannula. Rumen fluid was taken from each animal before feeding and every 4 hours thereafter until the 32nd hour. Samples were also taken at the 40th and 48th hours post-feeding. Rumen fluid pH was measured immediately after each sampling time. After the last sampling, 20 liters of rumen contents were removed from each animal and replaced with the same volume from donor animals. The steers were then fed the 50 C for five days.

A10255 Trial

After the baseline experiment, the four ruminally-fistulated steers were randomly allotted to four treatments in a 4×4 latin square design (Table 11). The treatments were level of A10255 as follows: 0. 0.22, 0.44 or 0.66 mg per kg BW.

Each period of the latin square consisted of the following: a) rumen evacuation and reinoculation (20 liters of rumen contents) on day 1 and start of twice a day feeding of the 50 C; b) morning feeding of the 50 C (half the amount consumed the day before) on day 4; c) feeding the 95 C (17 g per kg body weight) and start of rumen fluid sample collection on day 5; d) last sampling and rumen evacuation and reinoculation on day 7; e) feeding the 50 C from day 7 to 9. Day 10 is the start of a new period.

The appropriate amount of A10255 was weighed into gelatin capsule. Half of the daily dosage was put in the rumen of the animals during morning feeding and the other half during the afternoon. The animals were dosed with the drug from day 1 to day 6. However, the drug was not given from day 4 to day 6 during the first period; thus, period 1 was repeated as period 5 of the trial. All samples obtained in period 1 were disregarded.

Rumen Fluid Collection

On day 5, the steers were offered the 95 C and allowed to eat as much feed as they could in 2 hours. The feed remaining after 2 hours was placed manually in the rumen via the cannula. Rumen fluid samples were taken prior to and at 4, 8, 12, 16, 24, 28, 32, 40 and 48 hours after offering the 95 C. Rumen fluid was collected from each animal at each sampling time using a suction pump. The pump was used to create a vacuum in the collecting test tube and rumen fluid was allowed to flow via a plastic tube with suction strainer attached at the end. However, for Animal No. 2264, rumen fluid was collected by scooping samples of rumen contents and squeezing it through four layers of cheesecloth. This was due to the foamy condition of the rumen of this animal, making it difficult to leave the cannula open for a period of time.

After collecting approximately 200 ml of rumen fluid, the samples were taken to the laboratory and pH was measured. Approximately 120 ml of rumen fluid were centrifuged at 31,000 $\times$g for 25 minutes. About 10 ml of the supernatant was set aside and osmotic pressure was measured in duplicate using Wescor 5500 Vapor Pressure osmometer. The rest of the supernatant (about 90 ml) was placed in plastic cups with 1 ml of 37% HCl added and stored frozen until analyzed.

Volatile Fatty Acid Analysis

Two ml of rumen fluid and 0.5 ml of 5% metaphosphoric acid were mixed in test tube and centrifuged at 4,000 $\times$g for 10 minutes. A portion of the clear supernatant was placed in a vial and capped. Volatile fatty acid analysis was done using a Hewlett-Packard 5840A gas chromatograph using a packed glass column (2 mm internal diameter) containing Supelco 1220 packing. Carrier gas ($N_2$) flow was 20 ml/min and injection, column and detector temperatures were 170, 135 and 225° C., respectively.

Lactate Analysis

Ten ml rumen fluid was deproteinized by addition of 1 10 volume 6N perchloric acid, mixed and centrifuged at 10,000 $\times$g for 15 minutes. The supernatant was pipetted and made akaline by addition of 1/10 volume of 6N KOH. The pH was adjusted between 9 to 10 using 6N KOH. The precipitate was removed by centrifugation at 10,000 $\times$g for 15 minutes. The supernatant was decanted and stored frozen until analyzed. D-lactate was analyzed using the procedure of Brandt et al. (Brandt, R. B., S. A. Sieget, M. G. Waters and M. H. Bloch, 1980, Spectrophotometric assay of D(−)lactate in plasma, *Anal. Biochem.*, 102:39). L-lactate was analyzed using the procedure of Gutman and Wahlefeld (Gutman, I. and A. W. Wahlefeld, 1974, L(+)lactate determination with lactate dehydrogenase and NAD. In: H. Bergmeyer (ed.), Methods of enzymatic analysis, Vol. 3, Academic Press, N.Y.).

Glucose and $NH_3$-N Analysis

Glucose and $NH_3$-N content of rumen fluid were determined using an automated glucose oxidase method (Dahlquist, Arne, 1964, Method for assay of intestinal disaccharides, *Anal. Biochem.*, 7:18) and an automated adaptation of the indophenol method of McCullough (McCullough, H., 1967, The determination of ammonia in whole blood by a direct colorimetric method, *Clin. Chim. Acta*, 17:297), respectively.

Statistical Analysis

Analysis of variance in a latin square design with split plot of sampling time was used to analyze all data. Linear, quadratic and cubic effect of A10255 level and sampling time were determined. Least square means were calculated using the procedures described in SAS (SAS, 1982, SAS User's Guide, Statistical Analysis System Institute, Inc., Cary, N.C.).

RESULTS AND DISCUSSION

Preliminary Experiment

Animal Nos. 1385, 1383, 1384 and 2262 consumed 11.45, 11.05, 9.00 and 7.74 kg DM of the 95 C, respectively. This corresponds to 18.35, 18.02, 17.64 and 17.32 g 95 C per kg body weight. The lowest pH was 4.14 observed 20 hours post-feeding for animal No. 1383 (Table 12). Ruminal pH increased to about 6 at the last sampling time. The drop in pH to less than 5 indicates that the animals were acidotic but were able to recover without any assistance. Based on the pH response, 17 g of 95 C per kg body weight was used in the subsequent trial.

A10255 Trial

There was a significant cubic effect of A10255 level on ruminal pH (Table 13). The low and high levels of drug had higher pH than the control, while the medium level had the lowest pH. At 20 hours post-feeding, all animals had pH below 6 but those animals given the low and high dose of drug had pH above 6 by hour 24 and had the highest pH 48 hours after feeding. The drug may not be very effective in controlling pH drop but it helped the animal to come back to normal pH faster than without the drug. The same trends were observed for rumen pH osmotic pressure (Table 14) but in opposite direction.

D(+), L(−) and Total Lactate

Lactate levels of rumen fluid taken after hour 28 were nil; thus, they were not included in the statistical analysis. The low and high doses of A10255 lowered the ruminal concentration of D(−) lactate (Table 15), L(+) lactate (Table 16) and total lactate (Table 17), but the decrease was not statistically significant. However, lactate level at hour 20 was nil for the low and high doses of drug, while considerable amount was measured for the control treatment. The results suggest that the low and high doses of A10255 did not prevent lactate production but speed up the metabolism or disappearance of lactate in the rumen.

Total Volatile Fatty Acid and Organic Acid

Total organic acid (TOA) is the sum of total volatile fatty acid (TVFA) and total lactate. The low and high doses of A10255 had significantly lower TOA (Table 18) and TVFA (Table 19) than the control treatment. Likewise, the decline in the concentration of acids in the rumen was faster for the low and high doses of drug compared to control.

Acetate (A), Propionate (P) and A-P Ratio

The low and high levels of A10255 significantly decreased acetate level (Table 20) but slightly increased propionate (Table 21). This resulted in a significantly lower A-P ratio (Table 22) for the low and high levels of drug compared to control. The results suggest that the effect of the drug was mainly on acetate and not on propionate production.

The different doses of A10255 had no significant effect on butyrate, isobutyrate, valerate and isovalerate (Tables 23, 24, 25 and 26, respectively).

Glucose and NH$_3$-N Concentration

Glucose levels for rumen fluid collected from hour 4 to 16 were used in the statistical analysis, since the rest of the samples had no detectable glucose. The highest dosage of A10255 resulted in the lowest concentration of glucose in the rumen fluid (Table 27). However, large variation in the data resulted in no significant effect of A10255 on glucose level in rumen fluid. Likewise, rumen fluid NMH$_3$-N concentration in the rumen fluid (Table 28) was not significantly affected by A10255.

CONCLUSION

The results of the trial indicate that while A10255 was not able to prevent acidosis, it did speed up the recovery of the animal after the onset of acidosis.

TABLE 11
Experimental layout of A10255 trial.

| Animal No. | Periods |  |  |  |
|---|---|---|---|---|
|  | 1 | 2 | 3 | 4 |
|  | A10255 levels, mg/kg body weight |  |  |  |
| 1385 | 0 | .22 | .66 | .44 |
| 1383 | .22 | .44 | 0 | .66 |
| 1384 | .44 | .66 | .22 | 0 |
| 2264 | .66 | 0 | .44 | .22 |

TABLE 12
Rumen fluid pH of steers during the preliminary experiment

| Sampling Time, h | Animal Number |  |  |  |
|---|---|---|---|---|
|  | 1385 | 1383 | 1384 | 2264 |
| 0 | 7.17 | 6.98 | 7.16 | 7.08 |
| 4 | 5.88 | 5.64 | 5.60 | 7.03 |
| 8 | 5.24 | 4.94 | 5.16 | 6.16 |
| 12 | 4.93 | 4.44 | 4.38 | 5.41 |
| 16 | 4.60 | 4.21 | 4.20 | 4.90 |
| 20 | 4.75 | 4.14 | 4.37 | 4.59 |
| 24 | 4.96 | 4.21 | 4.67 | 4.63 |
| 28 | 5.27 | 4.38 | 4.74 | 4.87 |
| 32 | 5.96 | 4.66 | 5.75 | 5.10 |
| 40 | 6.84 | 5.94 | 6.34 | 6.03 |
| 48 | 6.54 | 6.87 | 6.72 | 6.94 |

TABLE 13
Effect of A10255 level and sampling time on rumen fluid pH.

| Sampling Time, h | A10255 Levels, mg/kg BW |  |  |  | Mean[a] |
|---|---|---|---|---|---|
|  | 0 | .22 | .44 | .66 |  |
| 0 | 6.84[c] | 6.90 | 6.78 | 6.96 | 6.87[d] |
| 4 | 6.38 | 6.42 | 6.41 | 6.59 | 6.45 |
| 8 | 5.57 | 5.85 | 5.50 | 5.77 | 5.67 |
| 12 | 5.28 | 5.30 | 5.04 | 5.38 | 5.25 |
| 16 | 5.17 | 5.23 | 4.74 | 5.31 | 5.11 |
| 20 | 5.35 | 5.69 | 5.10 | 5.63 | 5.44 |
| 24 | 5.61 | 6.30 | 5.19 | 6.02 | 5.78 |
| 28 | 5.91 | 6.10 | 5.80 | 6.01 | 5.96 |
| 32 | 6.15 | 6.41 | 5.79 | 6.20 | 6.13 |
| 40 | 6.16 | 6.58 | 6.41 | 6.76 | 6.48 |
| 48 | 6.54 | 6.87 | 6.72 | 6.94 | 6.76 |
| Mean[b] | 5.90[e] | 6.15 | 5.77 | 6.14 |  |

[a]Significant linear, quadratic and cubic effects of sampling time, P < .01.
[b]Significant cubic effect of treatment level, P < .05.
[c]Standard error of interaction means = .16.
[d]Standard error = .08.
[e]Standard error = .10.

TABLE 14
Effect of A10255 level and sampling time on rumen fluid osmotic pressure.

| Sampling Time, h | A10255 Levels, mg/kg BW |  |  |  | Mean[a] |
|---|---|---|---|---|---|
|  | 0 | .22 | .44 | .66 |  |
|  | mmol/kg |  |  |  |  |
| 0 | 259[c] | 262 | 257 | 262 | 260[d] |
| 4 | 294 | 310 | 280 | 278 | 290 |
| 8 | 286 | 307 | 324 | 293 | 302 |
| 12 | 317 | 304 | 356 | 319 | 324 |
| 16 | 330 | 318 | 383 | 318 | 337 |
| 20 | 324 | 283 | 341 | 289 | 309 |
| 24 | 324 | 247 | 343 | 274 | 297 |
| 28 | 294 | 251 | 284 | 271 | 275 |
| 32 | 270 | 251 | 284 | 273 | 269 |
| 40 | 261 | 242 | 258 | 257 | 254 |
| 48 | 252 | 259 | 249 | 265 | 256 |
| Mean[b] | 292[e] | 276 | 305 | 282 |  |

[a]Significant linear, quadratic and cubic effects of sampling time, P < .01.
[b]Significant cubic effect of treatment level, P < .05.
[c]Standard error of interaction means = 18.
[d]Standard error = 9.
[e]Standard error = 6.

TABLE 15
Effect of A10255 level and sampling time on rumen fluid D(−)-lactate level.

| Sampling Time, h | A10255 Levels, mg/kg BW |  |  |  | Mean[a] |
|---|---|---|---|---|---|
|  | 0 | .22 | .44 | .66 |  |
|  | mM |  |  |  |  |
| 4 | .62[b] | .23 | .23 | .16 | .31[c] |
| 8 | .33 | 1.78 | 1.58 | .40 | 1.02 |
| 12 | 4.78 | 6.79 | 14.18 | 10.93 | 9.17 |
| 16 | 10.55 | 17.32 | 21.40 | 11.75 | 15.25 |
| 20 | 10.71 | 6.86 | 14.28 | 7.06 | 9.72 |
| 24 | 9.01 | 0 | 9.45 | .01 | 4.62 |
| 28 | .60 | .02 | 0 | .01 | .16 |
| Mean | 5.23[d] | 4.71 | 8.73 | 4.33 |  |

[a]Significant quadratic effect of sampling time, P < .01.
[b]Standard error of interaction means = 4.07.
[c]Standard error = 2.04.
[d]Standard error = 2.44.

TABLE 16
Effect of A10255 level and sampling time on rumen fluid L(+)-lactate level.

| Sampling Time, h | A10255 Levels, mg/kg BW |  |  |  | Mean[a] |
|---|---|---|---|---|---|
|  | 0 | .22 | .44 | .66 |  |
|  | mM |  |  |  |  |
| 4 | .24[b] | .22 | .28 | .13 | .22[c] |
| 8 | .47 | 1.46 | 1.53 | .58 | 1.01 |
| 12 | 7.25 | 10.24 | 22.84 | 10.34 | 12.67 |
| 16 | 14.10 | 18.22 | 38.50 | 16.80 | 21.90 |
| 20 | 14.12 | 9.93 | 21.78 | 11.53 | 14.34 |
| 24 | 11.74 | 0 | 15.36 | .01 | 6.78 |
| 28 | 1.03 | .01 | .03 | 0 | .27 |
| Mean | 6.99[d] | 5.73 | 14.33 | 5.63 |  |

[a]Significant quadratic effect of sampling time, P < .01.
[b]Standard error of interaction means = 5.52.
[c]Standard error = 2.76.
[d]Standard error = 4.03.

TABLE 17
Effect of A10255 level and sampling time on rumen fluid total lactate level.

| Sampling Time, h | A10255 Levels, mg/kg BW |  |  |  | Mean[a] |
|---|---|---|---|---|---|
|  | 0 | .22 | .44 | .66 |  |
|  | mM |  |  |  |  |
| 4 | .86[b] | .46 | .52 | .28 | .53[c] |
| 8 | .80 | 3.24 | 3.11 | .98 | 2.03 |
| 12 | 12.03 | 17.03 | 37.02 | 21.28 | 21.84 |
| 16 | 24.65 | 35.53 | 59.90 | 28.56 | 37.16 |
| 20 | 24.84 | 16.79 | 36.06 | 18.59 | 24.07 |
| 24 | 20.74 | 0 | 24.80 | .02 | 11.39 |
| 28 | 1.64 | .02 | .03 | .01 | .42 |

TABLE 17-continued

Effect of A10255 level and sampling time on rumen fluid total lactate level.

| Sampling Time, h | A10255 Levels, mg/kg BW | | | | Mean[a] |
|---|---|---|---|---|---|
| | 0 | .22 | .44 mM | .66 | |
| Mean | 12.22[d] | 10.44 | 23.06 | 9.96 | |

[a]Significant quadratic effect of sampling time, P < .01.
[b]Standard error of interaction means = 9.39.
[c]Standard error = 4.69.
[d]Standard error = 6.45.

TABLE 18

Effect of A10255 level and sampling time on total organic acid.

| Sampling Time, h | A10255 Levels, mg/kg BW | | | | Mean[a] |
|---|---|---|---|---|---|
| | 0 | .22 | .44 mM | .66 | |
| 0 | 79.15[c] | 76.75 | 82.78 | 67.26 | 76.48[d] |
| 4 | 106.35 | 122.62 | 111.52 | 99.92 | 110.10 |
| 8 | 160.82 | 142.42 | 179.60 | 153.36 | 159.05 |
| 12 | 166.66 | 153.73 | 197.66 | 152.57 | 167.66 |
| 16 | 170.28 | 167.78 | 203.78 | 140.63 | 170.54 |
| 20 | 142.42 | 131.59 | 141.11 | 119.78 | 133.73 |
| 24 | 136.10 | 106.16 | 165.92 | 110.67 | 129.71 |
| 28 | 120.16 | 103.26 | 100.34 | 101.80 | 106.39 |
| 32 | 105.26 | 88.56 | 95.64 | 99.39 | 96.46 |
| 40 | 96.70 | 87.50 | 94.46 | 77.66 | 89.08 |
| 48 | 88.64 | 70.55 | 70.12 | 63.64 | 73.24 |
| Mean | 124.50[e] | 113.69 | 131.17 | 107.88 | |

[a]Significant linear, quadratic and cubic effects of sampling time, P < .01.
[b]Significant cubic effect of treatment level, P < .05.
[c]Standard error of interaction means = 13.75.
[d]Standard error = 6.87.
[e]Standard error = 5.30.

TABLE 19

Effect of A10255 level and sampling time on total volatile fatty acid.

| Sampling Time, h | A10255 Levels, mg/kg BW | | | | Mean[a] |
|---|---|---|---|---|---|
| | 0 | .22 | .44 mM | .66 | |
| 0 | 79.12[c] | 76.74 | 82.77 | 67.25 | 76.47[d] |
| 4 | 105.49 | 122.17 | 111.01 | 99.64 | 109.58 |
| 8 | 160.02 | 139.18 | 176.49 | 152.38 | 157.02 |
| 12 | 154.64 | 136.70 | 160.64 | 131.30 | 145.82 |
| 16 | 145.63 | 131.95 | 143.88 | 112.08 | 133.38 |
| 20 | 117.59 | 114.80 | 105.06 | 101.20 | 109.66 |
| 24 | 115.36 | 106.16 | 141.12 | 110.66 | 118.33 |
| 28 | 118.52 | 103.24 | 100.32 | 101.80 | 105.97 |
| 32 | 102.24 | 88.54 | 95.60 | 99.38 | 96.44 |
| 40 | 96.64 | 87.48 | 94.42 | 77.64 | 89.04 |
| 48 | 88.61 | 70.55 | 70.10 | 63.62 | 73.22 |
| Mean | 116.71[e] | 107.05 | 116.49 | 101.54 | |

[a]Significant linear, quadratic and cubic effects of sampling time, P < .01.
[b]Significant cubic effect of treatment level, P < .05.
[c]Standard error of interaction means = 13.44.
[d]Standard error = 6.72.
[e]Standard error = 3.95.

TABLE 20

Effect of A10255 level and sampling time on rumen fluid acetate level.

| Sampling Time, h | A10255 Levels, mg/kg BW | | | | Mean[a] |
|---|---|---|---|---|---|
| | 0 | .22 | .44 mM | .66 | |
| 0 | 53.54[c] | 52.46 | 54.38 | 44.94 | 51.33[d] |
| 4 | 69.96 | 78.62 | 70.86 | 61.60 | 70.26 |
| 8 | 102.38 | 83.75 | 107.32 | 87.62 | 95.27 |
| 12 | 95.62 | 79.02 | 100.90 | 75.00 | 87.63 |
| 16 | 90.18 | 72.98 | 91.21 | 61.18 | 78.88 |
| 20 | 72.61 | 59.27 | 56.01 | 52.58 | 60.12 |
| 24 | 69.78 | 50.79 | 80.74 | 56.53 | 64.46 |
| 28 | 66.32 | 45.88 | 49.61 | 50.99 | 53.20 |
| 32 | 52.22 | 39.64 | 42.62 | 48.84 | 45.83 |
| 40 | 48.27 | 43.35 | 37.56 | 35.42 | 41.15 |
| 48 | 43.62 | 36.67 | 30.67 | 32.50 | 35.86 |
| Mean[b] | 69.50[e] | 58.40 | 65.62 | 55.20 | |

[a]Significant linear, quadratic and cubic effects of sampling time, P < .01.
[b]Significant linear and cubic effect of treatment level, P < .05.
[c]Standard error of interaction means = 8.04.
[d]Standard error = 4.02.
[e]Standard error = 2.93.

TABLE 21

Effect of A10255 level and sampling time on rumen fluid propionate level.

| Sampling Time, h | A10255 Levels, mg/kg BW | | | | Mean[a] |
|---|---|---|---|---|---|
| | 0 | .22 | .44 mM | .66 | |
| 0 | 13.53[b] | 13.08 | 15.80 | 12.47 | 13.72[c] |
| 4 | 18.17 | 23.74 | 22.17 | 21.42 | 21.38 |
| 8 | 27.36 | 29.81 | 37.00 | 41.21 | 33.84 |
| 12 | 26.40 | 29.34 | 24.62 | 34.30 | 28.66 |
| 16 | 21.86 | 26.43 | 20.78 | 31.08 | 25.04 |
| 20 | 16.29 | 26.46 | 12.54 | 24.50 | 19.94 |
| 24 | 16.24 | 24.93 | 21.90 | 25.66 | 22.18 |
| 28 | 23.36 | 24.86 | 17.68 | 23.78 | 22.42 |
| 32 | 24.28 | 23.12 | 22.22 | 22.92 | 23.13 |
| 40 | 23.22 | 23.35 | 31.94 | 20.79 | 24.83 |
| 48 | 23.22 | 18.54 | 22.41 | 15.82 | 20.00 |
| Mean | 22.27[d] | 23.97 | 22.64 | 24.90 | |

[a]Significant quadratic and cubic effects of sampling time, P < .01.
[b]Standard error of interaction means = 3.98.
[c]Standard error = 1.99.
[d]Standard error = 1.04.

TABLE 22

Effect of A10255 level and sampling time on acetate-propionate ratio.

| Sampling Time, h | A10255 Levels, mg/kg BW | | | | Mean[a] |
|---|---|---|---|---|---|
| | 0 | .22 | .44 mM | .66 | |
| 0 | 4.05[c] | 4.12 | 3.50 | 3.66 | 3.83[d] |
| 4 | 3.89 | 3.38 | 3.21 | 2.92 | 3.35 |
| 8 | 3.83 | 2.92 | 2.90 | 2.16 | 2.93 |
| 12 | 4.42 | 2.69 | 4.44 | 2.27 | 3.46 |
| 16 | 7.22 | 2.81 | 5.89 | 2.62 | 4.64 |
| 20 | 6.58 | 2.32 | 6.39 | 2.56 | 4.46 |
| 24 | 5.15 | 2.09 | 4.04 | 2.32 | 3.40 |
| 28 | 2.84 | 1.94 | 2.89 | 2.36 | 2.51 |
| 32 | 2.48 | 1.81 | 2.37 | 2.22 | 2.22 |
| 40 | 2.26 | 2.04 | 1.49 | 1.80 | 1.90 |
| 48 | 2.03 | 2.04 | 1.46 | 2.07 | 1.90 |
| Mean[b] | 4.07[e] | 2.55 | 3.51 | 2.45 | |

[a]Significant linear and quadratic effects of sampling time, P < .05.
[b]Significant cubic effect of treatment level, P < .05.
[c]Standard error of interaction means = .80.
[d]Standard error = .40.
[e]Standard error = .33.

TABLE 23

Effect of A10255 level and sampling time on rumen fluid butyrate level.

| Sampling Time, h | A10255 Levels, mg/kg BW | | | | Mean[a] |
|---|---|---|---|---|---|
| | 0 | .22 | .44 mM | .66 | |
| 0 | 7.94[b] | 7.18 | 8.22 | 6.07 | 7.35[c] |
| 4 | 11.48 | 12.88 | 10.55 | 10.30 | 11.30 |
| 8 | 22.15 | 18.84 | 23.25 | 15.96 | 20.05 |
| 12 | 25.76 | 22.88 | 27.02 | 16.35 | 23.00 |
| 16 | 27.62 | 26.73 | 25.58 | 15.61 | 23.88 |
| 20 | 23.71 | 23.64 | 29.11 | 14.03 | 22.62 |
| 24 | 23.94 | 23.84 | 30.80 | 20.84 | 24.85 |

TABLE 23-continued

Effect of A10255 level and sampling time on rumen fluid butyrate level.

| Sampling Time, h | A10255 Levels, mg/kg BW | | | | Mean[a] |
|---|---|---|---|---|---|
| | 0 | .22 | .44 mM | .66 | |
| 28 | 22.74 | 24.64 | 24.77 | 19.62 | 22.94 |
| 32 | 18.88 | 18.34 | 21.39 | 18.81 | 19.35 |
| 40 | 16.68 | 12.86 | 14.25 | 13.14 | 14.23 |
| 48 | 14.59 | 9.21 | 9.03 | 9.36 | 10.55 |
| Mean | 19.59[d] | 18.28 | 20.36 | 14.55 | |

[a]Significant quadratic and cubic effects of sampling time, P < .01.
[b]Significant error of interaction means = 4.65.
[c]Standard error = 2.33.
[d]Standard error = 2.01.

TABLE 24

Effect of A10255 level and sampling time on rumen fluid isobutyrate level.

| Sampling Time, h | A10255 Levels, mg/kg BW | | | | Mean[a] |
|---|---|---|---|---|---|
| | 0 | .22 | .44 mM | .66 | |
| 0 | 1.44[b] | 1.43 | 1.45 | 1.30 | 1.40[c] |
| 4 | 1.66 | 1.88 | 1.78 | 1.92 | 1.81 |
| 8 | 1.92 | 1.67 | 2.02 | 2.09 | 1.92 |
| 12 | 1.58 | 1.21 | 1.43 | 1.42 | 1.41 |
| 16 | 1.25 | 1.01 | .80 | .72 | .94 |
| 20 | 1.16 | .87 | .60 | .78 | .85 |
| 24 | 1.17 | .97 | .66 | 1.03 | .96 |
| 28 | 1.23 | 1.42 | .88 | 1.16 | 1.17 |
| 32 | 1.22 | 1.40 | 1.08 | 1.80 | 1.38 |
| 40 | 1.73 | 1.93 | 1.61 | 1.71 | 1.75 |
| 48 | 1.45 | 1.64 | 1.84 | 1.38 | 1.58 |
| Mean | 1.44[d] | 1.40 | 1.28 | 1.39 | |

[a]Significant quadratic effect of sampling time, P < .01.
[b]Standard error of interaction means = .24.
[c]Standard error = .12.
[d]Standard error = .13.

TABLE 25

Effect of A10255 level and sampling time on rumen fluid valerate level.

| Sampling Time, h | A10255 Levels, mg/kg BW | | | | Mean[a] |
|---|---|---|---|---|---|
| | 0 | .22 | .44 mM | .66 | |
| 0 | .77[b] | .72 | .88 | .64 | .75[c] |
| 4 | 1.84 | 2.18 | 1.90 | 1.80 | 1.93 |
| 8 | 3.01 | 1.50 | 3.54 | 2.73 | 2.95 |
| 12 | 2.55 | 2.23 | 4.31 | 2.10 | 2.80 |
| 16 | 2.37 | 2.70 | 4.19 | 2.20 | 2.86 |
| 20 | 1.75 | 2.76 | 5.89 | 4.31 | 3.68 |
| 24 | 2.27 | 3.96 | 5.99 | 5.06 | 4.32 |
| 28 | 3.08 | 4.56 | 6.41 | 4.68 | 4.68 |
| 32 | 4.02 | 3.95 | 6.99 | 4.74 | 4.92 |
| 40 | 4.62 | 3.75 | 7.34 | 4.29 | 5.00 |
| 48 | 3.58 | 2.00 | 4.35 | 2.47 | 3.10 |
| Mean | 2.71[d] | 2.85 | 4.71 | 3.81 | |

[a]Significant linear quadratic effect of sampling time, P < .01.
[b]Standard error of interaction means = 1.08.
[c]Standard error = .54.
[d]Standard error = .52.

TABLE 26

Effect of A10255 level and sampling time on rumen field isovalerate level.

| Sampling Time, h | A10255 Levels, mg/kg BW | | | | Mean[a] |
|---|---|---|---|---|---|
| | 0 | .22 | .44 mM | .66 | |
| 0 | 1.92[b] | 1.87 | 1.83 | 1.84 | 1.86[c] |
| 4 | 2.40 | 2.87 | 2.56 | 2.61 | 2.61 |
| 8 | 3.21 | 2.61 | 3.28 | 2.80 | 3.00 |
| 12 | 2.75 | 2.03 | 2.39 | 2.15 | 2.33 |
| 16 | 2.37 | 2.12 | 1.34 | 1.29 | 1.78 |
| 20 | 2.08 | 1.81 | .92 | 1.20 | 1.50 |
| 24 | 1.96 | 1.68 | 1.03 | 1.56 | 1.56 |

TABLE 26-continued

Effect of A10255 level and sampling time on rumen field isovalerate level.

| Sampling Time, h | A10255 Levels, mg/kg BW | | | | Mean[a] |
|---|---|---|---|---|---|
| | 0 | .22 | .44 mM | .66 | |
| 28 | 1.80 | 1.89 | .97 | 1.58 | 1.56 |
| 32 | 1.64 | 2.09 | 1.32 | 2.28 | 1.84 |
| 40 | 2.12 | 2.25 | 1.72 | 2.30 | 2.10 |
| 48 | 2.16 | 2.50 | 1.80 | 2.11 | 2.14 |
| Mean | 2.22[d] | 2.16 | 1.75 | 1.97 | |

[a]Significant linear, quadratic and cubic effect of sampling time, P < .01.
[b]Standard error of interaction means = .36.
[c]Standard error = .18.
[d]Standard error = .30.

TABLE 27

Effect of A10255 level and sampling time on rumen fluid glucose content.

| Sampling Time, h | A10255 Levels, mg/kg BW | | | | Mean[a] |
|---|---|---|---|---|---|
| | 0 | .22 | .44 mg/dl | .66 | |
| 4 | 78.35[a] | 104.75 | 58.51 | 9.85 | 62.86[b] |
| 8 | 2.95 | 7.52 | 32.16 | 1.80 | 11.11 |
| 12 | 2.28 | 1.21 | 27.16 | 13.12 | 11.08 |
| 16 | .20 | 4.58 | 73.80 | 2.30 | 20.22 |
| Mean | 20.94[c] | 29.51 | 48.02 | 6.79 | |

[a]Standard error of interaction means = 36.09.
[b]Standard error = 18.04.
[c]Standard error = 11.71.

TABLE 28

Effect of A10255 level and sampling time on rumen fluid NH$_3$—N content.

| Sampling Time, h | A10255 Levels, mg/kg BW | | | | Mean[a] |
|---|---|---|---|---|---|
| | 0 | .22 | .44 mg/dl | .66 | |
| 0 | 62.92[b] | 5.34 | 6.18 | 6.61 | 6.26[c] |
| 4 | 11.50 | 13.46 | 11.46 | 12.94 | 12.34 |
| 8 | 11.29 | 8.87 | 12.52 | 5.27 | 9.49 |
| 12 | 5.55 | 5.15 | 9.40 | 5.04 | 6.28 |
| 16 | 4.23 | 5.82 | 8.84 | 7.14 | 6.51 |
| 20 | 6.07 | 6.04 | 10.70 | 6.27 | 7.27 |
| 24 | 7.22 | 1.63 | 13.86 | 7.42 | 7.53 |
| 28 | 8.11 | .63 | 12.46 | 6.33 | 6.88 |
| 32 | 8.70 | 2.46 | 5.80 | 6.32 | 5.81 |
| 40 | 3.80 | 5.37 | 2.46 | 5.58 | 4.30 |
| 48 | 4.38 | 6.35 | 3.32 | 6.44 | 5.12 |
| Mean | 7.07[d] | 5.56 | 8.82 | 6.85 | |

[a]Significant linear effect of sampling time, P < .01.
[b]Standard error of interaction means = 2.50.
[c]Standard error = 1.25.
[d]Standard error = 1.40.

In yet a further aspect of this invention, the A10255 complex and factors, and especially A10255 factor B, are useful in identifying Streptomyces species possessing a gene conveying thiostrepton resistance. Such a species may have naturally a thiostrepton-resistance gene or may have one after transformation with a plasmid or other cloning vector containing a thiostrepton-resistance gene. Thus, A10255B and the A10255 complex are interchangeable with the antibiotic thiostrepton to detect the thiostrepton resistance marker in recombinant DNA experiments with Streptomyces strains.

Specifically, protoplasts of the species S. fradiae, S. lividans, or S. griseofuscus are transformed with a plasmid (for example, pIJ702 or pHJL401) containing the thiostrepton-resistance conferring gene (C. J. Thompson et al., Nature, 286, p. 525-527 (1980)). The protoplasts are inoculated onto a solid medium suitable for cell wall generation, and incubated overnight (approximately 16 hours) at 29° C. A10255 is added to a soft agar overlay which is then poured on the surface of the plate containing the regenerating protoplasts. The amount of the A10255 antibiotic(s) used in the overlay must be sufficient to yield a concentration of approximately 50 µg/ml after application to the regeneration medium. The plates are then incubated for from seven to fourteen days at 29° C. to allow outgrowth of the subpopulation of cells containing the plasmid-borne thiostrepton-resistance conferring gene. Under these conditions, cells which have not received the plasmid do not grow. The A10255-resistant transformants are then transferred to medium containing 50 g/ml of A10255 which ensures maintenance of the plasmid carrying the thiostrepton-resistance conferring gene.

The A10255 complex, the individual factors and pharmaceutically-acceptable salts thereof of this invention are useful for the therapeutic or propylactic treatment of infections in warm-blooded animals caused by pathogenic bacteria. The antimicrobial compounds can be administered orally, parenterally (for example, intravenously, intramuscularly or subcutaneously) or as a topical ointment or solution in treating bacterial infections of warm-blooded animals.

A further aspect of this invention is the pharmaceutical compositions of the A10255 complex or the individual factors. These compositions are composed of a therapeutically active amount of the instant antibiotic compounds (i.e., the A10255 complex or factor B, factor C, factor E, factor F, factor G, factor H, or factor J separately or in combination) and a suitable vehicle. With regard to compositions for oral administration (for example tablets and capsules), the term "suitable vehicle" means common excipients such as binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose, and starch; fillers and carriers, for example corn starch, gelatin, lactose, sucrose, microcrystalline cellulose, kaolin, mannitol, di-calcium phosphate, sodium chloride, and aliginic acid, disintegrators such as croscarmellose sodium, microcrystalline cellulose, corn starch, sodium starch glycolate, aliginic acid, and mutable wetting agents such as sodium lauryl sulfate; and lubricants such as magnesium stearate and other metallic stearates, stearic acid, silicone fluid, talc, waxes, oils, and colloidal silica. Flavoring agents such as peppermint, oil of wintergreen, cherry flavoring or the like can also be used. It may be desirable to add a coloring agent to make the dosage form more appealing visually or to help identify the product. The tablets may also be coated by methods well known in the art.

The pharmaceutical compositions of the present invention may also be in the form of oral liquid preparations, which may be either a) aqueous or oily suspensions, solutions, emulsions or syrups; or b) a dry powder to be reconstituted with water or another suitable vehicle before use. When used in conjunction with such oral liquid preparations, the term "suitable vehicle" means conventional additives such as suspending agents, for example, sorbitol, syrup, methyl cellulose, glucose/sugar syrup, gelatin, hydroxyethylcellulose, carboxymethyl cellulose, or aluminum stearate gel; or hydrogenated edible oils, for example, almond oil, fractionated coconut oil, oily esters, propylene glycol or ethyl alcohol; and preservatives such as methyl or propyl p-hyroxybenzoates or sorbic acid.

The pharmaceutical composition can also be for intravenous (IV) use. Specifically, a water soluble form of the antibiotic compound can be dissolved in one of the commonly used intravenous fluids and administered by infusion. When used in conjunction with compositions for IV use, the term "suitable vehicle" means such fluids as physiological saline, Ringer's solution or 5% dextrose solution.

For intramuscular preparations a sterile formulation of a suitable salt form of the antibiotic compound (for example, the hydrochloride salt or sodium salt) can be formulated with a "suitable vehicle". Examples of such sterile formulations are a suitable salt form either dissolved in a pharmaceutical diluent (for example, Water-for-Injection) physiological saline, 5% glucose) or suspended in an aqueous base or a pharmaceutically acceptable oil base (for example, an ester of a long chain fatty acid such as ethyl oleate).

Topical compositions can be formulated with "suitable vehicles" such as hydrophobic or hydrophilic bases. Such bases include ointments, creams or lotions.

Veterinary pharmaceutical compositions of the antibiotic compounds may be administered in the feed or the drinking water of farm animals. Alternatively, the compounds can be formulated as intramammary preparations with "suitable vehicles" such as long- or quick-release bases.

The antibiotic compounds of the instant invention can also be formulated in unit dosage form in sterile vials, sterile plastic pouches containing a part with a septum, or sterile, hermetically sealed ampoules. The antibiotic compound (or a pharmaceutically-acceptable salt form thereof) may be a dry powder or in crystalline or lyophilized form. The amount of the antibiotic compound per unit dosage may vary from about 250 milligrams to about 10 grams.

A "therapeutically effective amount" of the antibiotic compounds of the present invention is from approximately 3.5 mg to about 50 mg of compound per kilogram of body weight. This amount generally totals from about 1 gram to about 27 grams per day for an adult human.

A further aspect of this invention is a method for treating or controlling infectious diseases caused by gram-positive and gram-negative organisms in warm-blooded animals. This method comprises administering to the animal an therapeutically effective amount of the instant antibiotic compounds. A typical daily dose for an adult human in this method is from about 1 gram to about 12 grams.

In practicing this method, the antibiotic compound can be administered in a single daily dose or in multiple doses per day. The treatment regime may require administration over extended periods of time, for example, for several days or for from two to three weeks. The amount administered per dose or the total amount administered will depend on such factors as the nature and severity of the infection, the age and general health of the patient, and the tolerance to the antibiotic compound of both the patient and the microorganism or microorganisms involved in the infection.

The following Examples are provided to further illustrate the invention. It is not intended that the invention be limited in scope by reason of any of the following examples.

EXPERIMENTAL SECTION

Example 1

The following medium was prepared for use in the agar slant culture of the A10255-producing microorganism:

| Production of A10255 Complex | |
| --- | --- |
| Ingredient | Amount (g/L) |
| Pre-cooked oatmeal | 60.0 |
| Yeast | 2.5 |
| $K_2HPO_4$ | 1.0 |
| KCl | 0.5 |
| $MgSO_4.7H_2O$ | 0.5 |
| $FeSO_4.7H_2O$ | 0.1 |
| Deionized water q.s. to | 1 liter |

The pH of the resultant medium was adjusted to pH 7.3 with aqueous sodium hydroxide. The medium was then autoclaved, yielding a sterilized medium with a pH of 6.7.

Spores of *S. gardneri*, NRRL 15537, were inoculated on a nutrient agar slant composed of the above sterilized medium. The inoculated slant was incubated for 7-10 days at a temperature of 30° C. The mature slant culture was then covered with calf serum and scraped with a sterile tool to loosen the spores and mycelia. The resultant suspension was transferred to small tubes and lyophilized for preservation. One lyophilized pellet was used to inoculate sterile vegetative culture medium (50 ml, contained in a 250 ml widemouth Erlenmeyer Flask) of the following composition:

| Ingredient | Amount (g/L) |
| --- | --- |
| Glucose | 15.0 |
| Dextrin | 20.0 |
| Soybean grits | 10.0 |
| Corn steep liquor | 10.0 |
| Yeast extract | 1.0 |
| $CaCO_3$ | 2.0 |
| Tap water q.s. to | 1 liter |

The pH of the medium was adjusted to 6.7 with aqueous sodium hydroxide. The medium was autoclaved, which raised the pH of the medium to between 6.8 and 7.0.

The inoculated vegetative medium was incubated for 48 hours at 30° C. on a shaker rotating through an arc two inches in diameter at 250 RPM. The resulting vegetative medium culture was used either to inoculate small fermenters (the inoculum being approximately 1% per volume of fermenter medium), or to inoculate second stage flasks for the production of a larger volume of inoculum.

Bump Medium

Two wide-mouth Erlenmeyer flasks (2 liter capacity) were charged with a medium (400 ml each) having the following composition:

| Ingredient | Amount (g/L) |
| --- | --- |
| Glucose | 15.0 |
| Dextrin | 20.0 |
| Soybean grits | 15.00 |
| Corn steep liquor | 10.0 |
| Yeast extract | 1.0 |
| $CaCO_3$ | 5.0 |

| -continued | |
| --- | --- |
| Ingredient | Amount (g/L) |
| Tap water q.s. to | 1 liter |

The medium in each Erlenmeyer flask was inoculated with the above vegetative culture. The volume of the inoculum totaled 2.5% of the volume of the medium in the Erlenmeyer flask. The inoculated medium was incubated at 30° C. for 24 hours on a rotary shaker at 250 RPM on a 10° angleboard to yield a "bump" culture.

Large Scale Fermentation

A portion of the above "bump" culture (800 ml) was used to inoculate the following medium (100 liter):

| Ingredient | Amoung (g/L) |
| --- | --- |
| Antifoam* | 0.200 |
| Propylene glycol (MW2000) | 2.000 ml |
| Glucose | 10.000 |
| Glycerol | 40.000 |
| Bacto-Peptone** | 10.000 |
| Casein | 10.000 |
| $NaH_2PO_4.H_2O$ | 0.100 |
| Blackstrap molasses | 40.000 |
| $CaCO_3$ | 2.500 |
| Tap water q.s. to | 100 liters |

*Dow-Corning Antifoam
**Meat hydrosylate (Difco Laboratories, Detroit, MI)

The medium was contained in a 165 liter fermenter. The pH of the medium was adjusted to 6.9 with 5N aqueous sodium hydroxide. The mixture was sterilized for 45 min. at 17-19 psi at 121° C. After the sterilization procedure the medium had pH 7.0. The sterilized medium was aerated with sterile air at the rate of 0.125 v/v/m, stirred with a conventional agitator at 200 RPM, and allowed to ferment for about 6 days at a temperature of 30° C.

Example 2

Isolation of the A10255 Antibiotic Complex

Whole fermentation broth (3780 L) was filtered using a filter aid (Hyflo Super-Cel, Johns-Manville Products Corp.). The press containing the mycelia was washed with 300 L of water, then the mycelia was extracted twice with acetone:water 4:1. The first extract was 900 L, the second 800 L. The extracts were combined and concentrated under reduced pressure to 450 L of an aqueous solution. The pH of the solution was adjusted to 3.0 with hydrochloric acid, then extracted three times with ethyl acetate (extract volumes were 165 L, 280 L, and 225 L respectively). The extracts and aqueous phase were analyzed for biological activity by a paper disc assay on agar plates seeded with *B. subtilis* ATCC 6633. The extracts were combined and concentrated to a volume of 23 L, under reduced pressure. The solids that had precipitated during concentration were collected by filtration and dried in vacuo to give 216 g of A10255 antibiotic complex assay: 90.7 g of activity). The filtrate was further concentrated to 900 ml and then filtered. The second precipitate was dried in vacuo to give 16.2 g of A10255 antibiotic complex (assay: 9.1 g activity).

Example 3

Separation of Factors from A10255 Antibiotic Complex

A10255 complex (20 g) was dissolved in chloroform:methanol (9:1, 400 ml total) and filtered. The filtrate was applied to a stainless steel column (8×100 cm) packed with 13-24 micron LPS-1 silica gel (4 l, Whatman Chemical Separation Inc., Clifton, N.J.). The column was part of a Chromatospac Prep-100 unit (Jobin Yvon, 16-18 Rue du Canal 91160, Longjumeau, France). A series of 240 ml fractions were collected from the column, which was eluted at a 60 ml/min flow rate first with a 9:1 chloroform:methanol mixture (7 L), then with a 3:1 chloroform:methanol mixture (15 L). During the chromatography the HPLC detector was set at 280 nm. All fractions were padded on agar plates seeded with *Micrococcus luteus* ATCC 9341 to detect biological activity. The following fractions were pooled:

| Fractions | Factors | Yield (gr.) |
|---|---|---|
| 11-23 | C,F | 0.68 |
| 30-63 | B,E | 6.50 |

The pool containing factors B and E was concentrated to 400 ml. The resultant precipitate was collected by filtration dried in vacuo to yield 5.86 g of material consisting primarily of factor B with a small amount of factor E. (assay: 3.6 g of activity). The supernatant from the precipitation was in turn concentrated. The concentrate was added to diethyl ether to give 0.64 g of a precipitate containing a similar mixture of factors B and E (assay:0.3 g of activity.

Example 4

Isolation of Antibiotic Factor A10255B

A 1.5 g portion of the material from Fractions 30-63 in the above Example 3 was dissolved in a mixture of tetrahydrofuran:water (35:65, 150 ml). The sample was applied to a stainless steel column (8×100 cm) packed with LP1-C18 reversed phase silica gel (4 l). (The silica gel was prepared by a procedure described in examples 6 and 7 of B. J. Abbott et al., U.S. Pat. No. 4,299,763, issued Nov. 10, 1981). The column was eluted at a flow rate of 60 ml/min. collecting 240 ml fractions with a tetrahydrofuran:water:disodium hydrogen phosphate mixture (3:7:0.05M, 12 l, pH 7.8 (phosphoric acid). The HPLC detector was set at 280 nm during the chromatography. Individual fractions were examined by analytical HPLC.

(The analytical HPLC was carried out on a 4.6×250 nm stainless steel column on a ultrasphere ODS 5 micron reversed phase material (altex Scientific Inc., Berkeley, Calif.). The column was eluted at a flow rate of 1 ml/min with a mixture of tetrahydrofuran:water:sodium hydrogen phosphate (1:2:0.05M, at pH 7.8 due to the addition of phosphoric acid). The detector was set at 254 nm during the chromatography.)

The fractions were pooled as follows:

| Fractions | Factors | Yield (gr.) |
|---|---|---|
| 17-23 | B (impure) | 150 ml |
| 24-35 | B (pure) | 200 ml |
| 38-45 | E | 100 ml |

The concentrated pool containing fractions 24-35 was diluted to 300 ml with deionized water and the pH of the resultant mixture was adjusted to pH 3.0 with phosphoric acid. The solution was extracted with a 7:3 mixture of chloroform:methanol. The extract was concentrated to dryness and chromatographed by HPLC. HPLC was carried out on a Michel-Miller high performance low pressure liquid chromatography ("HPLPLC") glass column (as described in K. Michel et al., U.S. Pat. No. 4,131,547, issued Dec. 26, 1978) containing a silica gel support (100-200 micron, Woelm Pharma). The column was eluted with a chloroform:methanol mixture (7:3). The HPLC monitor was set at 254 nm during the chromatography. The fractions containing the major UV chromophore were combined, concentrated in vacuo and lyophilized to give 659 mg Factor B.

Example 5

Purification of Antibiotic Facto A10255E

The pool of fractions 38-45 in Example 4 was combined with pools of similar composition from five additional chromatographies of the same manner as the one on the LP1-C18 support in the Example 4. The pH of the combined pools (800 ml) was adjusted to pH 3.0 with phosphoric acid. The combined pools were extracted with a 7:3 chloroform:methanol mixture (2×, 800 ml), then with an additional smaller amount 400 ml) of the solvent mixture. The extracts were combined, concentrated to dryness, and dissolved in 50 ml of a CHCl3:MeOH mixture (7:3, 500 ml). The solution was applied to a 5.1×42 cm Michel-Miller HPLPLC glass column containing a silica gel support (500 ml, 100-200 micron, Woelm). The column was eluted with a mixture of 7:3 (v:v) chloroform:methanol and the major UV chromophore (254 nm) was collected and taken to dryness to yield 349 mg of pure factor E.

Example 6

Purification of Antibiotic Factors C and F

The dried preparation (0.68 g) obtained from the pool of fractions 11-23 in Example 3 was combined with preparations obtained in a similar manner to total 3.03 g of solid. This material was dissolved in a mixture of tetrahydrofuran:water (6:4) and the solution chromatographed on reversed phase silica gel (4 l) in a stainless steel column (8×100 cm) eluted at a flow rate of 60 ml/min with a mixture of 3:7 tetrahydrofuran:water (39 l) monitored at 280 nm. The 480 ml fractions collected were padded on agar plates seeded with *Micrococcus luteus* ATCC 9341 to detect biological activity. Biologically active fractions were further analyzed by the analytical-scale HPLC system described in Example 4. The fractions were pooled as follows:

| Fractions | Factors | Yield (mg) |
|---|---|---|
| 28-37 | unknown | 186 |
| 40-50 | C (impure) | 373 |
| 51-55 | C (pure) | 302 |
| 56-62 | C (impure) | 70 |
| 66-75 | F (pure) | 56 |

Each pool was concentrated and the resultant precipitate was collected on a filter and dried in vacuo.

Example 7

The agar slant medium used in Example 1 was used to culture the A10255-producing microorganism NRRL 18260.

Accordingly, one lyophylized pellet from the above procedure was used to inoculate sterile vegetative culture medium (50 ml, contained in a 250 ml wide-mouth Erlenmeyer flask) of the following composition:

| Ingredient | Amount (g/L) |
| --- | --- |
| Trypticase soy broth | 30.0 |
| Enzyme-hydrolyzed casein (Universal Foods, Juneau, WI) | 5.0 |
| Glucose | 5.0 |
| Glycerol | 10.0 |
| Dextrin | 10.0 |
| CaCO$_3$ | 10.0 |
| Tap water q.s. to | 1 liter |

The pH of the medium was adjusted to 7.0 with aqueous sodium hydroxide before autoclaving.

The inoculated vegetative medium was incubated for 72 h at 30° C. on a shaker rotating through an arc two inches in diameter at 250 RPM. The resulting vegetative medium culture was used either to inoculate small fermenters (the inoculum being approximately 1% per volume of fermenter medium), or to inoculate second stage flasks for the production of a larger volume of inoculum.

Bump Medium

Two wide-mouth Erlenmeyer flasks (2 liter capacity) were charged with a medium (400 ml each) identical to the vegetative medium described above.

The medium in each Erlenmeyer flask was inoculated with the above vegetative culture. The volume of the inoculum totaled 2.5% of the volume of the medium in the Erlenmeyer flask. The inoculated medium was incubated at 30° C. for 48 hours on a rotary shaker at 250 RPM on a 10° angle from horizontal to yield a "bump" culture.

Large Scale Fermentation

A portion of the above "bump" culture (800 ml) was used to inoculate the following medium (100 liter):

| Ingredient | Amount (g/L) |
| --- | --- |
| Sag 471 | 0.2 |
| P-2000 | 0.1 ml |
| Glucose | 1.0 |
| NH$_4$Cl | 1.0 |
| Na$_2$SO$_4$ | 2.0 |
| ZnCl$_2$ | 0.019 |
| MgCl$_2$.6H$_2$O | 0.304 |
| FeCl$_3$ | 0.062 |
| MnCl$_2$.4H$_2$O | 0.035 |
| CaCl$_2$ | 0.06 |
| CuCl$_2$.2H$_2$O | 0.005 |
| KH$_2$PO$_4$* | 0.67 |
| Tap water q.s. to | 110 liters |

*Sterilized separately in deionized H$_2$O after being adjusted to pH 6.0 with KOH.

The medium was contained in a 165 liter fermenter. The mixture was steam sterilized by the application of 20 F$_o$ heating units (where 1 F$_o$ equals exactly one minute at 121° C.). After the sterilization procedure the medium had pH 8.3. The pH after KH$_2$PO$_4$ addition was 7.0. The sterilized medium was aerated with sterile air and stirred with a conventional agitator to maintain the dissolved oxygen level at 45% of air saturation at 5 psi above atmospheric pressure, and allowed to ferment for about 7–10 days at a temperature of 30° C.

During the large scale fermentation as outlined above, it was found to be efficacious to continuously "feed" the fermentation mixture with glucose at the rate of 5.7 g/l/day. Casein hydrolysate was also fed after 17 hours at 4.5 g/l/day. A lipid, such as ethyl caprate or methyl oleate, was also fed after about 22 hours at 1–2 ml/l/day.

Examples 8

Isolation of Antibiotic Factor A10255G

A 1.0 g portion of the antibiotic complex from Example 2 was dissolved into 2 l of H$_2$O:CH$_3$CN (4:1) at pH 6.0. This solution was applied to a Waters Prep 500 using a C18 cartridge column. The column was eluted using a shallow linear gradient of 4 lof (A) H$_2$O:CH$_3$CN:THF:HOAc (70:30:5:0.5) to 4 l of (B) H$_2$O:CH$_3$CN:THF:HOAc (65:35:5:0.5) at a flow rate of 250 ml per minute, collecting one fraction per minute. This was followed by 2 l of solvent (B). The column eluate was monitored at 280 nm. Seven additional runs were made using identical conditions. Pools containing a mixture of factors C and G were combined, the pH adjusted to 6.0 using 5N NaOH, diluted with an equal volume of water (to a total volume of 26 l) and chromatographed in two separate runs, using 13 l each time. These runs were also made on a C18 cartridge column on a Waters Prep 500. A linear gradient from 4 l of solvent (A) 0.05N NH$_4$OAc (pH 5.5):CH$_3$CN (75:25) to 4 of solvent (B) 60:40 was used for the chromatography, followed by 2 l of solvent (B). The flow rate used was 250 ml per minute and one fraction was collected each minute. Fractions containing mainly factor G were combined, diluted using an equal volume of water, and rechromatographed on a C18 cartridge column using a Prep 500. The following linear gradient was used: (A) 4 l of H$_2$O:CH$_3$CN:THF:HOAc (70:30:5:0.5) to (B) 4 l of (65:35:5:0.5), at the same flow rate described above. Fractions containing factor G only were combined and concentrated in vacuo to an aqueous solution. The precipitated factor G was then separated by centrifugation, washed with water, suspended in water and lyophilized to give 686 mg of factor G.

Example 9

Isolation of Antibiotic Factor A10255H

A 1.0 g portion of the antibiotic complex from Example 2 was dissolved into 2 l of H$_2$O:CH$_3$CN (4:1) at pH 5.0 and filtered through glass wool on a filter funnel. The solution was applied to a C18 cartridge column on a Waters Prep 500. The column was eluted using a linear gradient from 4 l of (A) H$_2$O:CH$_3$CN:THF:HOAc (70:30:5:0.5) to 4 l of (B) 65:35:5:0.5 at a flow rate of 250 ml per minute, collecting one fraction every minute. This was followed by 2 l of solvent (B).

The column eluate was monitored at 280 nm. Thirteen additional runs were made using identical conditions. All pools containing factor H were combined (17 l), concentrated and dried in vacuo to give 690 mg of crude factor H. This material was combined with 329 mg of a similar preparation, dissolved into 3 l of H$_2$O:CH$_3$CN:THF (75:20:5) at pH 6.0 and applied to a C18 cartridge column as described above. A linear gradient from 4 l of solvent (A) 0.05 M NH$_4$OH:CH$_3$CN (75:25) to 4 l of solvent (B) 0.05M NH$_4$OH:CH$_3$CN (60:40) was used for the chromatography. This was followed by 2 l of solvent (B). Flow rate and fraction volume were the same as described above. Fractions containing factor H were combined (750 ml), added to an equal volume of water and applied again to a C18 cartridge column as described above. The column was developed using a linear gradient from 4 l of (A) H$_2$O:CH$_3$CN:THF:HOAc (75:25:5:0.5) to 4 l of (B) H$_2$O:CH$_3$CN:THF:HOAc (60:40:5:0.5), collecting one 250 ml fraction every minute. The factor H containing fractions 23-29 were combined and concentrated in vacuo to a volume of 450 ml. The precipitated factor H was recovered by filtration, washed with water and dried in vacuo to give 285 mg of factor H.

Example 10

Isolation of Antibiotic A10255 Factor J

A 2.0 g portion of the antibiotic complex from Example 2 was dissolved into 40 ml of THF/H$_2$O (4:1) and applied to a C18 cartridge column on a Waters Prep 500. The column was eluted using a linear gradient from 4 l of (A) H$_2$O:CH$_3$CN:THF:HOAc (70:29.5:0.5) to 4 l of (B) 60:39.5:0.5 at a flow rate of 250 ml per minute. The column eluate was monitored at 280 nm. Four additional runs were made using identical conditions. All fractions containing factors H and J were combined, concentrated and dried in vacuo to give 1.6 g of a crude mixture of factors H and J.

A 100 mg sample of the above preparation was dissolved into 1 ml of THF:H20 (4:1) and applied to a C18 Rainin Dynamax 41.1 mm I.D. column (Rainin Instrument Co., Inc.). The column was conditioned using the mixture H$_2$O:CH$_3$OH:CH$_3$CN:HOAC (60:30:9.5:0.5). Solvents (A) H$_2$O:CH$_3$OH:CH$_3$CN:HOAC (60:30:9.5:0.5) and (B) 20:60:19.5:0.5 were used to develop the column, and the gradient run was from 35% (B) to 45% (B) in 120 minutes at a flow rate of 25 ml/minute. Three additional runs were made. Fractions containing pure factor J were combined, concentrated until precipitation was completed, filtered and dried in vacuo to give 82 mg of pure factor J.

Example 11

Feed Composition for Promoting Growth in Cattle

The A10255 complex or its individual factors can be administered orally to cattle by mixing an effective amount of the complex or factor with the feed. For example, one aspect of the invention is a standard feed ration of the composition:

| Ingredient | Amount |
| --- | --- |
| Corn Silage (whole plant, ears intact) | 50% |
| High Moisture Corn | 44%* |
| Supplement (total) | 6% | wherein the Supplement is composed of:

| Ingredient | Amount |
| --- | --- |
| Alfalfa Meal, (Dehydrated, 17%) | 12.00% |
| Soybean Oil Meal (Solvent Extracted) | 45.40% |
| Urea, Feed Grade | 5.00% |
| Dicalcium Phosphate | 8.00% |
| Salt | 10.00% |
| Calcium Carbonate | 11.00% |
| Trace Mineral Premix | 0.80% |
| Vitamin A + D3 Premix | 1.40% |
| Vitamin E Premix | 1.40% |
| Potassium Chloride | 5.00% |

Prior to administration, the standard ration was mixed with an A10255 complex-containing premix. The premix was composed of the following ingredients:

| Ingredient | Amount |
| --- | --- |
| Yellow Corn | 48.00% |
| Grit-O-Cobs 20/40 | 50.00% |
| Mineral Oil | 2.00% |
| | 100.00% |

The premix was first mixed with the A10255 complex at an application rate of, for example, either 275 mg/head/day or 550 mg/head/day (which for this particular experiment, translates to 28.6 and 61.7 g/ton, respectively). The A10255 complex-containing premix is then top-dressed (and subsequently mixed) with the above standard feed ration at an application rate of 0.35 lb/head/day.

We claim:

1. Antibiotic A10255 factor B, which has the formula:

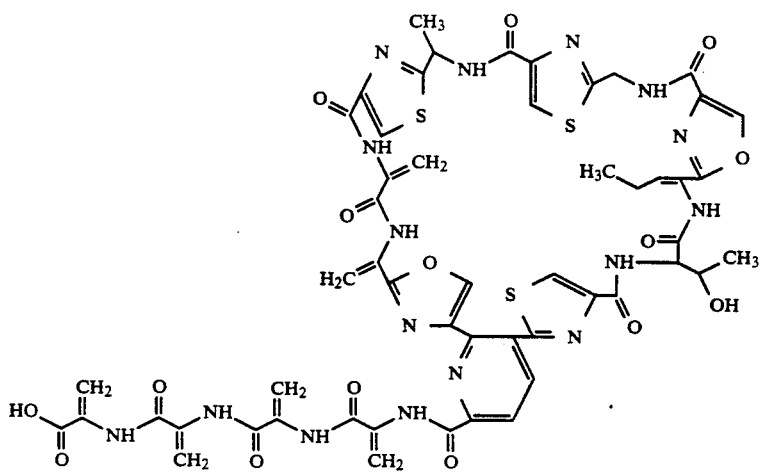

or a pharmaceutically-acceptable salt thereof.

2. Antibiotic A10255 factor C, which is a non-crystalline white to light-yellow powder possessing the following physical characteristics:

(a) An approximately, averaged elemental analysis of 49.18 percent carbon, 3.86 percent hydrogen, 17.89 percent nitrogen, 18.28 percent oxygen and 6.46 percent sulfur;

(b) A proton nuclear magnetic resonance spectrum in perdeutero dimethylsulfoxide at 360 MHz with signals at the following % values: 10.51, 10.08, 9.84, 9.57, 9.10, 8.88, 8.03, 7.94, 7.53, 5.15, 8.67, 8.59, 8.51, 8.49, 8.38, 8.25, 8.24, 6.57, 6.52, 6.38, 6.11, 5.91, 5.78, 5.74, 5.70, 5.65, 5.63, 5.44, 5.15, 4.79, 4.67, 4.63, 4.23, 2.21, 1.62, 1.11, 1.01;

(c) An infrared absorption spectrum as shown in FIG. 2;

(d) An ultraviolet absorption spectrum with an absorption maximum at 245 nm ($\epsilon = 63,000$) in neutral, acidic, and basic methanol;

(e) A molecular weight of approximately 1174 daltons, as determined by fast atom bombardment mass spectral analysis;

(f) Titratable groups measured in 66% aqueous dimethylformamide with pKa values of approximately 2.9 and 12;

(g) Contains approximately 758 millimoles/milligram of threonine and approximately 7,429 millimoles/milligram of ammonia equivalents, as determined by standard hydrolysis procedures with 6N hydrochloric acid;

(h) Is soluble in dimethylsulfoxide, dimethylformamide, pyridine, 1:1 (v:v) methylene chloride:methanol, and 4:1 (v:v) of tetrahydrofuran:water; or a pharmaceutically acceptable salt thereof.

3. Antibiotic A10255 factor E, which is a non-crystalline white to light-yellow powder having the following characteristics:

(a) An approximate averaged elemental analysis of 48.03 percent carbon; 3.91 percent hydrogen, 15.76 percent nitrogen, 17.09 percent oxygen and 5.63 percent sulfur;

(b) An infrared absorption spectrum in a potassium bromide pellet with significant absorption maxima at the following frequencies (in cm$^{-1}$): 3367, 3361, 2966, 1664, 1501, 1389, 1254, 1102, and 889;

(c) Titratable groups measured in 66% aqueous dimethylformamide with pKa values at approximately 4.85, 11.1, and 13.2;

(d) A molecular weight of about 1258 daltons as determined by fast atom bombardment mass spectroscopy;

(e) Is soluble in dimethylsulfoxide, dimethylformamide, pyridine, and an approximately 4:1 (v:v) mixture of tetrahydrofuran:water;

(f) Contains approximately 716 millimoles/milligram of threonine and approximately 8,580 millimoles of ammonia equivalent per milligram, as determined by hydrolysis with 6N hydrochloric acid;

(g) An ultraviolet absorption spectrum in acidic, basic and neutral methanol exhibiting an absorption maximum at 245 nm ($\epsilon = 77,000$);

(h) A proton nuclear magnetic resonance spectrum in perdeuterated dimethylsulfoxide at 270 MHz exhibiting signals at $\delta$ 10.54, 10.00, 9.94, 9.81, 9.60, 9.56, 9.45, 8.89, 8.84, 8.66, 8.59, 8.50, 8.47, 8.39, 8.25, 8.22, 8.10, 6.53, 6.50, 6.24, 5.95, 5.86, 5.84, 5.77, 5.64, 5.55, 5.52, 5.44, 5.10, 4.80, 4.66, 4.64, 4.22, 2.78, 1.60, 1.11 and 1.00;

or a pharmaceutically-acceptable salt thereof.

4. Antibiotic A10255 factor F, which is a non-crystalline white to light yellow powder possessing the following physical characteristics:

(a) An approximately, averaged elemental analysis of 49.65 percent carbon, 4.23 percent hydrogen, 17.11 percent nitrogen, 22.08 percent oxygen, and 7.78 percent sulfur;

(b) A proton nuclear magnetic resonance spectrum in perdeuterated dimethylsulfoxide at 360 MHz with signals at $\delta$ 10.51, 10.17, 9.88, 9.77, 9.54, 9.10, 8.90, 8.88, 8.66, 8.59, 8.51, 8.49, 8.38, 8.25, 8.24, 8.06, 7.94, 7.53, 6.56, 6.51, 6.27, 6.23, 6.12, 6.12, 5.96, 5.77, 5.76, 5.71, 5.71, 5.64, 5.62, 5.47, 5.14, 4.77, 4.65, 4.62, 4.20, 2.77, 2.48, 2.48, 1.58, 1.08, 0.98, and 0.98;

(c) An infrared absorption spectrum in potassium bromide with absorption maxima at 3369, 2943, 2907, 2846, 1663, 1588, 1519, 1493, 1425, 1337, 1288, 1251, 1151, 1110, 1083, 995, 927, 890, 807, 776, and 751 cm$^{-1}$;

(d) An ultraviolet absorption spectrum with an absorption maximum at 245 nm ($\epsilon = 71,500$) in neutral, acidic, and basic methanol;

(e) A molecular weight of approximately 1188 daltons, as determined by fast atom bombardment mass spectroscopy;

(f) A titratable group measured in 66% aqueous dimethylformamide at a pKa of 12.5;

(g) Contains approximately 735 millimoles/milligram of threonine and approximately 7,226 millimoles/milligram of ammonia equivalents, as determined by standard hydrolysis procedures with 6N hydrochloric acid;

(h) Is soluble in dimethylsulfoxide, dimethylformamide, pyridine, 1:1 (v:v) methylene chloride:methoanol, and 4:1 (v:v) of tetrahydrofuran:water; or a pharmaceutically acceptable salt thereof.

5. Antibiotic A10255 factor G which has the following structure:

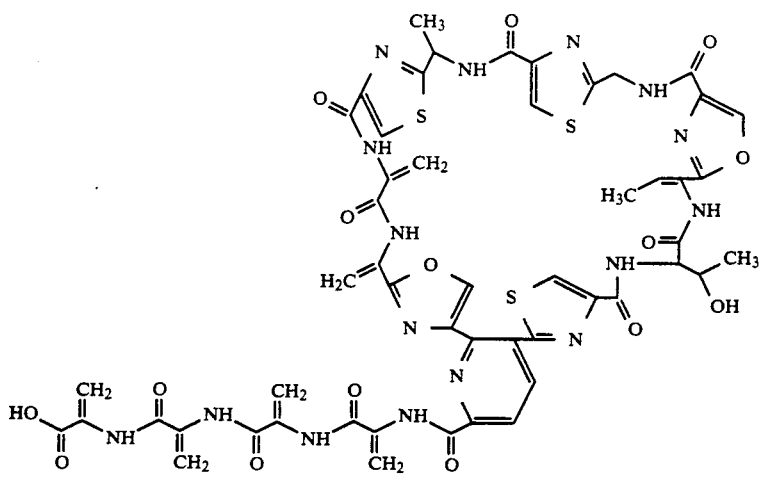

or a pharmaceutically-acceptable salt thereof.

6. A10255 factor J. which has the structure:

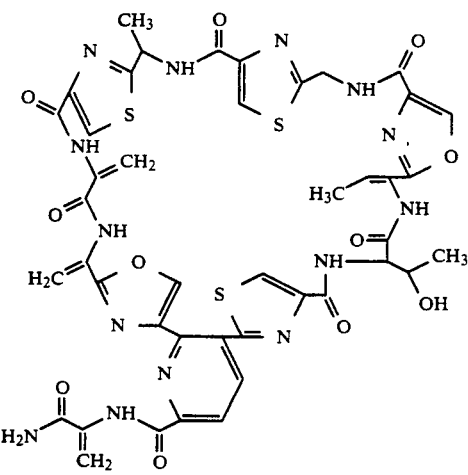

7. Antibiotic A10255 complex produced by cultivating *Streptomyces gardneri* NRRL 15537 or *Streptomyces gardneri* NRRL 18260, or A10255-producing mutant thereof, in an aqueous culture medium containing assimilable sources of carbohydrate, nitrogen, and inorganic salts under submerged aerobic fermentation conditions until the antibiotic A10255 complex is produced.

8. A pharmaceutical composition comprising a suitable vehicle and a therapeutically effective amount of A10255 complex, an A10255 factor chosen from the group consisting of A10255 factor B, A10255 factor C, A10255 factor E, A10255 factor F, A10255 factor G, A10255 factor H. or a mixture of one or more of said factors, or a pharmaceutically-acceptable salt thereof.

9. The pharmaceutical composition of claim 8 comprising a therapeutically effective amount of the A10255 complex.

10. The pharmaceutical composition of claim 8, comprising a therapeutically effective amount of an A10255 factor or factors selected from A10255 factors B, C, E, F, G, and H, or a pharmaceutically-acceptable salt thereof.

11. The pharmaceutical composition of claim 10 comprising a therapeutically effective amount of A10255 factor B or G.

12. A feed composition for increasing feed utilization efficiency in poultry, which comprises poultry feed and a feed-utilization-enhancing amount of the A10255 complex, an A10255 factor selected from the group of A10255 factors B, C, E, F, G, and H, or a combination of one or more of said factors, or a pharmaceutically-acceptable salt thereof.

13. A feed composition of claim 12 comprising a feed-utilization-enhancing amount of the A10255 complex.

14. A feed composition for increasing feed utilization efficiency and promoting growth in weanling pigs, which comprises swine feed and an effective amount of the A10255 complex, an A10255 factor selected from the group consisting of A10255 factor B, A10255 factor E, A10255 factor F, A10255 factor G, and A10255 factor H, or a combination of one or more of said factors, or a pharmaceutically-acceptable salt thereof.

15. A feed composition of claim 14, which comprises swine feed and an effective amount of the A10255 complex or a pharmaceutically-acceptable salt thereof.

16. A feed composition for increasing the feed utilization efficiency of cattle, which comprises cattle feed and an effective amount of the A10255 complex, an A10255 factor selected from the group consisting of A10255 factor B, A10255 factor C, A10255 factor E, A10255 factor F, A10255 factor G, and A10255 factor H, or a combination of one or more of said factors, or a pharmaceutically-acceptable salt thereof.

17. A feed composition of claim 16, which comprises cattle feed and an effective amount of the A10255 complex.

18. A method for increasing the feed utilization efficiency of cattle, which comprises administering to cattle an effective amount of the A10255 complex, an A10255 factor selected from the group consisting of A10255 factor B, A10255 factor C, A10255 factor E, A10255 F, A10255 factor G, and A10255 factor H, or a combination of one or more of said factors, or a pharmaceutically-acceptable salt thereof.

19. A method of claim 18, which comprises administering to cattle an effective amount of the A10255 complex or a pharmaceutically-acceptable salt thereof.

20. Antibiotic A10255 factor H, which is a non-crystalline white to light-yellow powder which is soluble in dimethylsulfoxide, dimethylformamide, pyridine, 1:1 (v:v) methylene chloride/methanol, and 4:1 (v:v) tetrahydrofuran:water, having the following physical characteristics:

a) an ultraviolet spectrum in neutral ethanol which shows a $\lambda_{max}$=244 nm ($\epsilon$=74,000); acidic solution, $\lambda_{max}$=245 nm ($\epsilon$=74,500); and basic solution, $\lambda_{max}$=211 nm ($\epsilon$=23,800); and b) a molecular weight of about 1160 as determined by fast atom bombardment mass spectroscopy;

c) a $^{13}$C nuclear magnetic resonance spectrum at 125 MHz in perdeuterated dimethylsulfoxide having the following signals:

| Resonance No. | Shift ($\delta$) | Multiplicity |
|---|---|---|
| 1 | 172.92 | S |
| 2 | 168.92 | S |
| 3 | 168.86 | S |
| 4 | 165.14 | S |
| 5 | 163.63 | S |
| 6 | 163.03 | S |
| 7 | 162.65 | S |
| 8 | 162.33 | S |
| 9 | 161.52 | S |
| 10 | 160.30 | S |
| 11 | 160.14 | S |
| 12 | 159.99 | S |
| 13 | 159.45 | S |
| 14 | 158.94 | S |
| 15 | 158.09 | S |
| 16 | 149.43* | S |
| 17 | 148.78 | S |
| 18 | 148.03 | S |
| 19 | 146.90 | S |
| 20 | 142.07 | D |
| 21 | 141.30 | D |
| 22 | 140.68 | D |
| 23 | 139.21 | S |
| 24 | 136.96 | S |
| 25 | 136.10 | S |
| 26 | 134.67 | S |
| 27 | 134.07 | S |
| 28 | 133.80 | S |
| 29 | 130.27 | S |
| 30 | 129.03 | S |
| 31 | 128.78 | D |
| 32 | 127.24 | D |
| 33 | 125.94 | D |
| 34 | 124.99 | D |
| 35 | 123.71 | S |
| 36 | 121.50 | D |
| 37 | 111.76 | T |
| 38 | 110.45 | T |
| 39 | 106.11 | T |
| 40 | 104.67 | T |
| 41 | 104.44 | T |
| 42 | 67.39 | D |
| 43 | 57.95 | D |
| 44 | 46.54 | D |
| 45 | 40.22 | T |
| 46 | 20.66 | Q |
| 47 | 20.34 | Q |
| 48 | 13.52 | Q |

*Doubly intense d) a $^1$H nuclear magnetic resonance spectrum in 500 MHz in perdeuterated dimethylsulfoxide having the following signals:

| Resonance No. | Shift | Multiplicity |
|---|---|---|
| 1 | 10.51 | S |
| 2 | 10.08 | S |
| 3 | 9.81 | S |
| 4 | 9.79 | S |
| 5 | 9.57 | S |
| 6 | 9.10 | S |
| 7 | 8.86 | T |
| 8 | 8.83 | D |
| 9 | 8.68 | S |
| 10 | 8.60 | D |
| 11 | 8.51 | S |
| 12 | 8.50 | D |
| 13 | 8.39 | S |
| 14 | 8.25 | D |
| 15 | 8.24 | S |
| 16 | 8.03 | D |
| 17 | 7.94 | S |
| 18 | 7.53 | S |
| 19 | 6.56 | S |
| 20 | 6.53 | S |
| 21 | 6.48 | Q |
| 22 | 6.12 | S |
| 23 | 5.96 | S |
| 24 | 5.80 | S |
| 25 | 5.78 | S |
| 26 | 5.74 | S |
| 27 | 5.72 | S |
| 28 | 5.65 | S |
| 29 | 5.64 | S |
| 30 | 5.44 | DQ |
| 31 | 5.15 | D |
| 32 | 4.80 | DD |
| 33 | 4.68 | DD |
| 34 | 4.63 | DD |
| 35 | 4.24 | BS |
| 36 | 1.78 | D |
| 37 | 1.62 | D |
| 38 | 1.10 | D; and | e) an infrared spectrum with the following absorption maxima: 3390, 3139, 2932, 1662, 1598, 1531, 1520, 1496, and 1428 cm$^{-1}$.

* * * * *